United States Patent [19]

Matsuo, deceased et al.

[11] Patent Number: 4,673,739

[45] Date of Patent: * Jun. 16, 1987

[54] 4-CARBAMOYLOXYMETHYL-1-SULFO-2-OXOAZETIDINE DERIVATIVES AND THEIR PRODUCTION

[75] Inventors: Taisuke Matsuo, deceased, late of Ibaraki, Japan, by Michiko Matsuo, heir; Michihiko Ochiai, Suita; Shoji Kishimoto, Takarazuka, both of Japan

[73] Assignee: Takeda Chemical Industries, Ltd., Osaka, Japan

[ * ] Notice: The portion of the term of this patent subsequent to Feb. 25, 2003 has been disclaimed.

[21] Appl. No.: 778,219

[22] Filed: Sep. 18, 1985

Related U.S. Application Data

[60] Division of Ser. No. 499,801, May 31, 1983, Pat. No. 4,572,801, which is a continuation-in-part of Ser. No. 405,592, Aug. 5, 1982, which is a continuation-in-part of Ser. No. 326,938, Dec. 3, 1981.

[30] Foreign Application Priority Data

Dec. 5, 1980 [WO] PCT Int'l Appl. .... PCT/JP80/00297
Apr. 30, 1981 [WO] PCT Int'l Appl. .... PCT/JP81/00103
Aug. 21, 1981 [WO] PCT Int'l Appl. .... PCT/JP81/00183
Sep. 24, 1981 [WO] PCT Int'l Appl. .... PCT/JP81/00252
Apr. 30, 1982 [JP] Japan ................................ 57-73728
May 31, 1982 [JP] Japan ................................ 57-93463

[51] Int. Cl.[4] ................. C07D 205/08; C07D 417/02; A61K 31/425
[52] U.S. Cl. ................................................. 540/355
[58] Field of Search ...................... 260/239 A, 245.4; 540/355

[56] References Cited

U.S. PATENT DOCUMENTS 4,200,572 4/1980 Gleason et al. ............... 260/239 A
4,225,586 9/1980 Imada et al. .................... 424/117
4,229,436 10/1980 Imada et al. .................... 424/117

FOREIGN PATENT DOCUMENTS 887428 3/1981 Belgium .
3239157A1 10/1984 Fed. Rep. of Germany .
2071650 3/1978 United Kingdom .
2091724 7/1979 United Kingdom .

OTHER PUBLICATIONS

Imada et al., Nature, vol. 289, pp. 590–591 (1981).
Sykes et al., Nature, vol. 291, pp. 489–491 (1981).
12th International Congress of Chemotherapy, Florence, Italy, Jul. 19–24, 1981, pp. 55–56.
Sykes et al., Journal of Antimicrobial Chemotherapy, (1981) 8 Suppl. E 1–16.
Sykes et al., Chemical Abstracts, 95, 217370S (1981).
Matsuo et al., Chemical Abstracts, 95, 97566M (1981).

*Primary Examiner*—Mark L. Berch
*Attorney, Agent, or Firm*—Wenderoth, Lind & Ponack

[57] ABSTRACT

Compounds of the formula

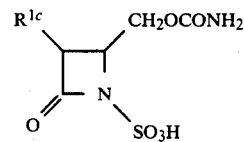

are useful as intermediates in preparing 1-sulfo-2-oxoazetidine compounds having the carbamoyloxymethyl group at the 4-position. The final product compounds have antimicrobial and/or β-lactamase-inhibitory activity and are of value as drugs for human beings and domesticated animals.

11 Claims, 1 Drawing Figure

4-CARBAMOYLOXYMETHYL-1-SULFO-2-OXOAZETIDINE DERIVATIVES AND THEIR PRODUCTION

This application is a division of application Ser. No. 499,801, filed May 31, 1983, (now U.S. Pat. No. 4,572,801) which application is a continuation-in-part of application Ser. No. 405,592, filed Aug. 5, 1982, which application is a continuation-in-part of application Ser. No. 326,938, filed Dec. 3, 1981.

This invention relates to novel azetidine derivatives and to the methods for producing them. In particular there are provided novel 1-sulfo-2-oxoazetidine compunds which have antimicrobial activity and/or β-lactamase-inhibitory activity.

The present inventors, as a result of their intensive research for the purpose of obtaining novel and useful 1-sulfo-2-azetidinone derivatives, have found that either sulfonation of a compound of the formula

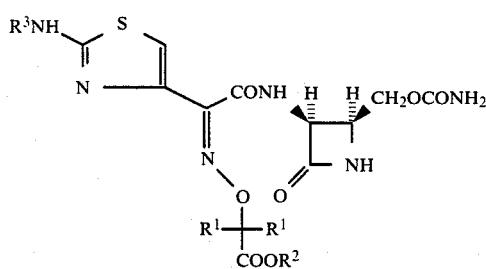

wherein $R^1$ is a hydrogen atom or a lower alkyl group, $R^2$ is a hydrogen atom or an ester residue and $R^3$ is an amino-protecting group, or a salt thereof followed by removal of the protective group and, if necessary, the ester residue, or reaction of (3S,4S)-cis-3-amino-4-carbamoyloxymethyl-2-azetidinone-1-sulfonic acid (hereinafter called "compound [A]") or a salt or ester thereof with a carboxylic acid of the formula

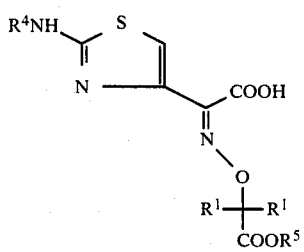

wherein $R^1$ is as defined above, $R^4$ is a hydrogen atom or an amino-protecting group and $R^5$ is an ester residue, of a functional derivative thereof followed by removal of the protective group and, if necessary, the ester residue gives a 1-sulfo-2-azetidinone derivative of the formula

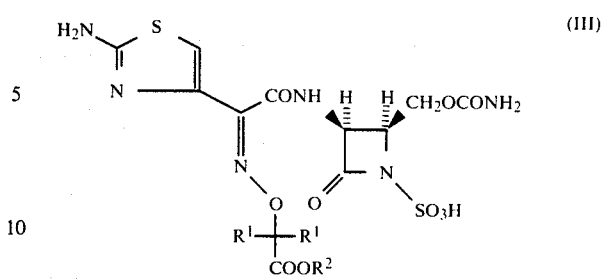

wherein the symbols are as defined hereinabove, or a salt or ester thereof, which derivative has the (3S,4S)-configuration and that the thus-obtained compound (III) or a salt or ester thereof exhibits strong antibacterial activity gainst gram-negative bacteria including *Pseudomonas aeruginosa* and is very stable against β-lactamases produced by microorganisms and have a good distribution to body tissues. These findings have led to the present invention.

Figure 1:
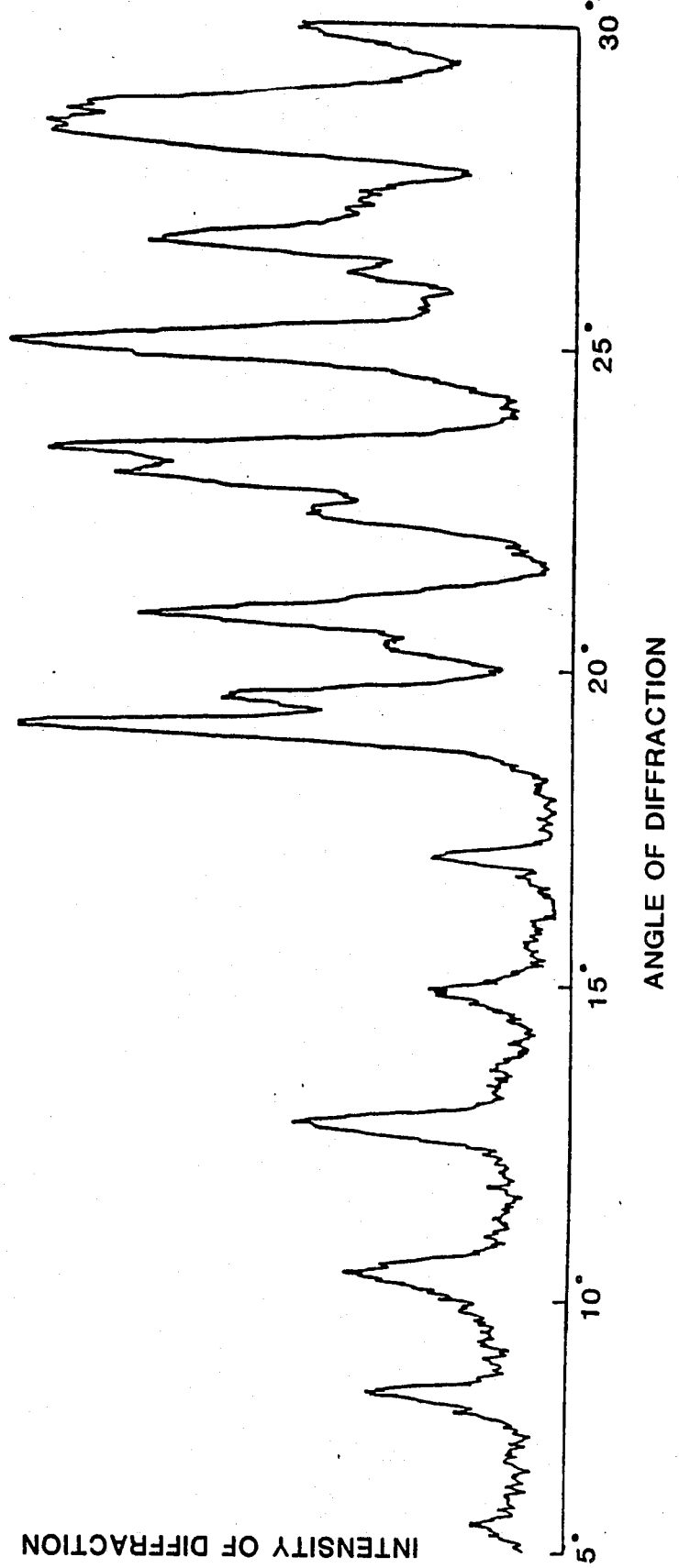
FIG. 1 is a powder X-ray diffraction pattern of the product of Example 5.

The invention provides:
(1) A compound [III] or a salt or ester thereof;
(2) A method of producing compound [III] or a salt or ester thereof which comprises sulfonating compound [I] or a salt thereof and then removing the protective group and, if necessary, the ester residue; and
(3) A method of producing compound [III] or a salt or ester thereof which comprises reacting compound [A] or a salt or ester thereof with carboxylic acid [II] or a functional derivative thereof and then removing the protective group and, if necessary, the ester residue.

Referring to the above formulas [I], [II] and [III], the lower alkyl group represented by $R^1$, which preferably contains 1–4 carbon atoms, is, for example, methyl, ethyl, n-propyl, n-butyl, isopropyl or isobutyl.

The ester residue represented by $R^2$ in the above formulas [I] and [III] or $R^5$ in formula [II] includes those biologically active ester residues that are capable of increasing the blood concentration and the duration of efficacy, among others, such as, for example, α-($C_{1-4}$)alkoxy($C_{1-4}$)alkyl groups (e.g. methoxymethyl, ethoxymethyl, isopropoxymethyl, α-methoxyethyl, α-ethoxyethyl), ($C_{1-4}$)alkylthiomethyl groups (e.g. methylthiomethyl, ethylthiomethyl, isopropylthiomethyl), α-($C_{2-6}$)acyloxy($C_{1-4}$)alkyl groups (e.g. pivaloyloxymethyl, α-acetoxyethyl) and α-($C_{1-4}$)alkoxycarbonyloxy($C_{1-4}$)alkyl groups (e.g. ethoxycarbonyloxymethyl, α-ethoxycarbonyloxyethyl) as well as those ester residues that are commonly used as carboxyl-protecting groups, such as, for example, tert-butyl, benzhydryl, benzyl, p-nitrobenzyl, p-methoxybenzyl p-nitrophenyl, β-trimethylsilylethyl, β,β,β-trichloroethyl and trialkylsilyl (e.g. tert-butyldimethylsilyl, isopropyldimethylsilyl). As the ester residues serving as carboxyl-protecting groups, tert-butyl, benzhydryl and p-nitrobenzyl, for instance, are especially preferable.

The amino-protecting group represented by $R^3$ and $R^4$ in the above formulas [I] [II], respectively, is conveniently selected from among those which are commonly used for the same purpose in the synthesis of antimicrobial β-lactam compounds. Thus, for example, such amino-protecting groups as acyl groups (e.g. formyl, acetyl, monochloroacetyl, dichloroacetyl, trichloroacetyl, trifluoroacetyl), esterified carboxyl groups (e.g. tert-butoxycarbonyl, 2-cyanoethoxycarbonyl, $\beta,\beta,\beta$-trichloroethoxycarbonyl, $\beta$-trimethylsilylethoxycarbonyl, benzyloxycarbonyl, p-nitrobenzyloxycarbonyl, p-methoxybenzyloxycarbonyl, diphenylmethyloxycarbonyl) and further trityl and trialkylsilyl. Especially preferable among these are formyl, monochloroacetyl and trityl, for instance.

The desired compound according to the invention, namely compound [III], may be used either in the free acid form with respect to the sulfo and carboxyl groups or, in the conventional manner, in the form of a salt with a nontoxic cation such as sodium or potassium or with a basic amino acid (e.g. arginine, ornithine, lysine, histidine) or a polyhydroxyalkylamine (e.g. N-methylglucamine, diethanolamine, triethanolamine, tris(hydroxymethyl)aminomethane), for instance. Also the amino group in the 2-position of the thiazole ring may be used either in the free amino form or, in the conventional manner, in the form of a salt with an organic acid (e.g. acetic, tartaric or methanesulfonic acid) or an inorganic acid (e.g hydrochloric, hydrobromic, sulfuric or phosphoric acid) or further an acidic amino acid (e.g. aspartic or glutamic acid). Furthermore, the carboxyl group may be used in the form of an ester with such biologically active ester residue as mentioned above for $R^2$ and $R^5$.

Although the compound of the invention [III], may be used in the form of a racemic mixture, it is the optically active form having the (3S,4S)-configuration that has an essential antimicrobial activity. Therefore, the present invention provides compounds [III] having the (3S,4S)-configuration, salts and esters thereof and methods of producing them.

The objective compounds [III] or salts or esters thereof are valuable antibiotics active against gram-negative bacteria, among others. They are used as drugs for humans and domestic animals. More particularly, they are safely used as antimicrobial agents for treating a variety of bacterial infections. The compounds of the invention [III] or salts or esters thereof are added as bactericides to feed to be given to animals for the preservation thereof. Furthermore, they may be used as bactericides for destroying and inhibiting the growth of hazardous bacteria on, for instance, medical and dental devices and as industrial microbiocides for inhibiting the growth of hazardous bacteria in water-based paints, paper mill white water and other aqueous compositions in concentrations of 0.1–100 parts of compounds [III] or salts or esters thereof per million parts of the aqueous compositions.

Compounds [III] of the invention or salts or esters may be used in various pharmaceutical compositions either alone or in combination with other active ingredients. The pharmaceutical compositions may take the form of capsules, tablets, powders, solutions, suspensions or elixirs. They may be administered orally, intravenously or intramuscularly.

The tablets for oral administration may contain usual vehicles such as binders (e.g. syrup, gum arabic, gelatin, sorbitol, gum tragacanth, polyvinylpyrrolidone), fillers (e.g. lactose, other saccharides, corn starch, calcium phosphate, sorbitol, glycine), lubricants (e.g. magnesium stearate, talc, polyethylene glycol, silica), disintegrants (e.g. potato starch) and available humectants (e.g. sodium lauryl sulfate). The tablets may be coated by the methods well known in the art. The liquid preparations for oral use may take the form of aqueous or oleaginous suspensions, solutions, emulsions, syrups, elixirs, etc., or may be dried products to be dissolved in water or other appropriate solvents prior to use. Such liquid preparations may contain suspending agents (e.g. sorbitol syrup, methylcellulose, glucose/saccharide syrup, gelatin, hydroxyethylcellulose, carboxymethylcellulose, aluminum stearate), hydrogenated edible oils (e.g. almond oil, fractionated coconut oil, oily esters), propylene glycol or ethyl alcohol, preservatives (e.g. methyl or propyl p-hydroxybenzoate, sorbic acid), etc. As the suppository bases, there may be used, for instance, cacao butter and other glycerides.

The compositions for injection may be supplied in the unit dosage form such as an ampule or a container with a preservative added. Said compositions may be in the form of suspensions, solutions or emulsions in oleaginous or aqueous solvents and may contain adequate auxiliaries such as suspending agents, stabilizers and/or dispersing agents. The active ingredients may also be formulated in the powder form so that the compositions may be reconstructed with an appropriate solvent, for example, sterilized pyrogen-free water, prior to use.

Furthermore, adequate forms for absorption through the nasal and laryngeal mucosa or the bronchial tissue may also be formulated, for instance, powders, liquid sprays or inhalants, lozenges and throat paints. For the eye or ear treatment, the active ingredients may be used in the liquid or semisolid form as capsules or drops. They may further be formulated in compositions for external use using hydrophobic or hydrophilic ointment, cream, lotion, paint, powder or other bases.

Furthermore, the pharmaceutical compositions may contain other ingredients than vehicles, such as, for example, stabilizers, binders, antioxidants, preservatives, lubricants, suspending agents, viscosity modifiers and flavoring agents. For broader antibacterial spectra, the compositions may also contain other active ingredients.

For use in domestic animals, the active ingredients may be formulated in intrammary compositions in bases adequate for prolonged action or rapid release.

Compounds [III] of the invention or salts or esters thereof may be used as the therapeutic agents for bacterial infections in the treatment of, for example, respiratory tract infections, urinary tract infections, suppurative diseases, bile tract infections, intestinal infections, gynecological infections and surgical infections in mammals. The daily dose depends on condition of the patient to be treated, body weight of the host, route of administration (parenteral administration being suited for treating general infections and oral administration for treating intestinal infections) and frequency of administration, among others. Generally, the daily oral dose is about 15–300 mg of the active ingredient per kilogram of body weight of the patient in single or multiple application. The adequate daily dose for a human adult is about 10 to about 150 mg of the active ingredient per kg of body weight, preferably in 2 to 4 divided doses with each single dose of about 2.5 to about 75 mg/kg, and parenteral administration is adequate.

The compositions containing compounds [III] or salts or esters thereof may be administered in several solid or liquid unit dosage forms administrable orally. The liquid or solid unit dosage form compositions contain the active substance in concentrations of 0.5–99%, preferably about 10–60%. The compositions generally contain about 15–1500 mg of the active ingredient. However, doses within the range of about 250–1000 mg are generally suited.

The desired compounds [III] of the invention or salts or esters thereof can be produced by sulfonating compounds [I] or salts thereof followed by removing the protective group and, if necessary, the ester residue.

The starting compounds [I] are used in the free form or in the form of salts such as mentioned for compounds [III]. The sulfonation reaction involves the introduction of a sulfo group into the 1-position of compounds [I] or salts thereof by reacting compounds [I] or salts thereof with sulfuric anhydride (sulfur trioxide) or a functional derivative thereof, for instance. The functional derivative of sulfuric anhydride includes, for example, such adducts as sulfuric anhydride-pyridine, sulfuric anhydride-picoline, sulfuric anhydridelutidine, sulfuric anhydride-N,N-dimethylformamide, sulfuric anhydride-dioxane, sulfuric anhydride-trimethylamine and sulfuric anhydride-chlorosulfonic acid as well as such mixtures as sulfuric acid-acetic anhydride. In the above sulfonation reaction, sulfuric anhydride or a functional derivative thereof is used in an amount of about 1–10 moles, preferably about 1–5 moles, per mole of compound [I]. The reaction temperature is about $-20°$ C. to about $80°$ C., preferably $0°$–$60°$ C. The use of a solvent is generally preferred and the solvent includes water and commonly used organic solvents such as ethers (e.g. dioxane, tetrahydrofuran, diethyl ether), esters (e.g. ethyl acetate, ethyl formate), halogenated hydrocarbons (e.g. chloroform, dichloromethane), hydrocarbons (e.g. benzene, toluene, n-hexane) and amides (e.g. N,N-dimethylformamide, N,N-dimethylacetamide), either alone or in admixture. Depending on the kind of starting material [I], sulfonating agent, reaction temperature and kind of solvent, the reaction generally proceeds to completion in a few scores of minutes to a few scores of hours. In some cases, several days may be required for completion of the reaction. After the reaction, the reaction product can be recovered by any of purification and separation procedures known per se, for example, solvent extraction, recrystallization and chromatography, in any desired purity. It is also possible to use the reaction mixture itself as the starting material in the next step.

The thus-obtained sulfonation products, upon removal of the protective group and, if necessary, the ester residue, give the desired products. The ester residue to be removed if necessary includes those residues generally used as the carboxyl-protecting groups and easily removable after the sulfonation reaction and may be removed simultaneously with the removal of the amino-protecting group $R^3$ or before or after the removal of said amino-protecting group. Some of the above-mentioned amino-protecting and carboxyl-protecting groups, depending on the kind thereof, may be removed under the above-mentioned sulfonation reaction conditions, and, in such a case, no separate protective group removal step is required. The removal of the amino-protecting and carboxyl-protecting groups can be effected, for example, with an acid or base, or by reduction, depending on the protective group species. When an acid is used, the acid which should be selected depending on the protective group species and other factors is, for example, such an inorganic acid as hydrochloric, sulfuric or phosphoric acid, such an organic acid as formic, acetic, trifluoroacetic, propionic, benzenesulfonic or p-toluenesulfonic acid, or an acid-form ion exchange resin. When a base is used, the base which should be selected depending on the protective group species and other factors is, for example, such an inorganic base as a hydroxide or carbonate of an alkali metal (e.g. sodium, potassium) or an alkaline earth metal (e.g. calcium, magnesium), such an organic base as a metal alkoxide, an organic amine or a quaternary ammonium salt, or a base-form ion exchange resin. When a solvent is used for the protective group removal, the solvent is in most cases a hydrophilic organic solvent, water or a mixture thereof. When the removal is effected by reduction, the reduction is carried out, depending on the protective group species and other factors, by using such a metal as tin or zinc or such a metal compound as chromium dichloride or chromium acetate together with such an organic or inorganic acid as acetic, propionic or hydrochloric acid, or catalytically in the presence of a metal catalyst for catalytic reduction. The catalyst for use in the catalytic reduction includes among others platinum catalysts such as platinum wire, platinum sponge, platinum black, platinum oxide and colloidal platinum, palladium catalysts such as palladium sponge, palladium black, palladium oxide, palladium-on-barium sulfate, palladium-on-barium carbonate, palladium-on-carbon, palladium-on-silica gel and colloidal palladium, and nickel catalysts such as reduced nickel, nickel oxide, Raney nickel and Urushibara nickel. When a combination of a metal and an acid is used, a compound of such a metal as iron or chromium on one hand and such an inorganic acid as hydrochloric acid or such an organic acid as formic, acetic or propionic acid on the other are used. The reductive method is generally carried out in a solvent. In catalytic reduction, for instance, alcohols such as methanol, ethanol, propyl alcohol and isopropyl alcohol as well as ethyl acetate or the like are used frequently. In performing the method using a metal and an acid, the solvent is most frequently water or acetone or the like, and, when the acid is a liquid, the acid itself may be used as the solvent. The reaction in the acid-treatment, base-treatment or reduction procedure is generally carried out with or without cooling or warming. For removing a silyl-containing protective group, a fluoride ion-containing compound such as tetrabutylammonium fluoride or potassium fluoride may also be used. When the amino-protecting group is monochloroacetyl, removal thereof can easily be performed by using, for example, thiourea or sodium N-methyl-dithiocarbamate.

The desired compounds of the invention can also be produced by reacting compound [A] or a salt or ester thereof with carboxylic acid [II] or a functional derivative thereof followed by removing the protective group and, if necessary, the ester residue.

Compounds [A] may be used either in the free form or in the form of salts or esters such as mentioned for compounds [III]. Carboxylic acids [II] are used either in the free acid form or in the form of functional derivatives, with respect to the carboxyl group. The functional derivatives or carboxylic acids [II] are, for example, acid halides, acid anhydrides, active amides, active esters and active thioesters. Examples of these functional derivatives are given below:

(1) Acid halides:

Such acid halides as acid chlorides and acid bromides are used.

(2) Acid anhydrides:

Such acid anhydrides as mixed acid anhydrides with, for example, monoalkyl carbonic acids, aliphatic carboxylic acids (e.g. acetic, pivalic, valeric, isovaleric, trichloroacetic acid) or aromatic carboxylic acids (e.g. benzoic acid) as well as symmetric acid anhydrides.

(3) Active amides:

Amides with pyrazole, imidazole, 4-substituted imidazole, dimethylpyrazole and benzotriazole, for instance, are used.

(4) Active esters:

Such active esters as methyl ester, ethyl ester, methoxy-methyl ester, propargyl ester, 4-nitrophenyl ester, 2,4-dinitrophenyl ester, trichlorophenyl ester, pentachlorophenyl ester, mesylphenyl ester and esters with 1-hydroxy-1H-2-pyridone, N-hydroxysuccinimide and N-hydroxyphthalimide, among others, are used.

(5) Active thioesters:

Thioesters, for example, with such heterocycle thiols as 2-pyridinethiol and 2-benzothiazolylthiol.

Preferable thioesters are compounds of the formula

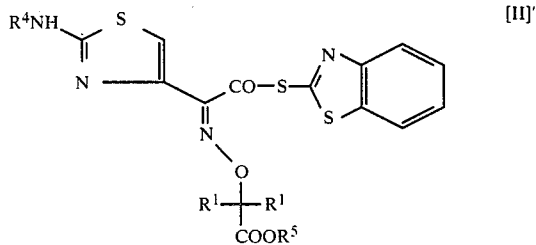
[II]' wherein the symbols are as defined hereinabove. Said thioesters may be produced by reacting the compound [II] with a heterocyclic thiol as mentioned above. A heterocyclic thiol is used in an amount of 1 to 4 moles per mole of [II]. The reaction may be conducted in an inactive organic solvent having no hydroxy group in its molecule, in the presence of a phosphine or phosphite. As such a phosphine, use is made of aryl phosphines such as triphenyl phosphine, and as such a phosphite, use is made of tri-lower alkyl phosphites such as trimethyl phosphite or triethyl phosphite. The phosphine or phosphite is preferably used in an amount of 1 to 2 moles per 1 mole of [II]. The inactive organic solvent for use in this reaction includes halogenated hydrocarbons such as dichloromethane, chloroform, etc., nitriles such as acetonitrile, propionitrile, etc., esters such as ethyl acetate, isopropyl acetate, etc. Among them, nitriles such as acetonitrile, for instance, are especially preferable. The used amount of the solvent may be 10-50 times (weight) of that of the compound [II]. In order to dissolve [II], a base may be added to the solvent. For example, an organic base such as pyridine, N-methylmorpholine, triethylamine, etc. may be used as the base. The used amount of the base is 1-2.5 moles per 1 mole of [II]. The reaction temperature is normally −30° C.–50° C., preferably −20° C.–25° C., more preferably −5° C.-5° C. The reaction time is usually about 1-20 hours. Genrally, thus obtained active thioester of the compound [II] forms precipitation and so may be isolated by filtration. If necessary, before the filtration, putting the obtained reaction mixture into water, extracting the aqueous solution with such an organic solvent as mentioned above and then adding n-hexane, etc. to the extract in this order may be conducted to get the active thioester of the compound [II] as precipitates.

A functional derivative adequate for each specific instance is selected from among the above-mentioned derivatives depending on the kinds of $R^1$, $R^4$ and $R^5$ in carboxylic acid [II].

In practicing the above method, compound (A) or a salt or ester thereof is first reacted with carboxylic acid [II] or a functional derivative thereof in a proportion of 1 mole of the former to at least 1 mole, preferably 1-4 moles of the latter. The reaction is generally carried out in a solvent. The solvent includes water, acetone, dioxane, acetonitrile, methylene chloride, chloroform, dichloroethane, tetrahydrofuran, ethyl acetate, N,N-dimethylformamide, N,N-dimethylacetamide, pyridine and other common organic solvents inert to the reaction. Hydrophilic solvents may be used in admixture with water. When carboxylic acid [II] is used in the free form, the reaction is preferably carried out in the presence of a condensing agent, such as, for example, N,N'-dicyclohexylcarbodiimide, N-cyclohexyl-N'-morpholinoethylcarbodiimide, N-cyclohexyl-N'-(4-diethylaminocyclohexyl)carbodiimide or N-ethyl-N'-(3-dimethylaminopropyl)carbodiimide. The reaction may also be conducted in the presence of such a base as an alkali metal carbonate, a trialkylamine (e.g. trimethylamine, triethylamine, tributylamine, N-methylmorpholine, N-methylpiperidine), N,N-dialkylaniline N,N-dialkylbenzylamine, pyridine, picoline, lutidine, 1,5-diazabicyclo[4,3,9]non-5-ene, 1,4-diazabicyclo[2,2,2]octane or 1,8-diazabicyclo[5,4,4]undecene-7. When the base or condensing agent is a liquid, it may also serve as the solvent. The reaction temperature is not critical but, generally, the reaction is carried out in many cases with cooling or at room temperature. The reaction is complete in several minutes to a few scores of hours. The reaction product can be recovered and purified by per se known methods, such as concentration, pH adjustment, phase transfer, solvent extraction, crystallization, recrystallization, fractional distillation and chromatography. The reaction product may also be used as the starting material in the next step in the form of a reaction mixture, without isolating said product.

The product yielded by the above acylation reaction is then used as the starting material in the step of removing the protective group and, if necessary, the ester residue. This removal step is carried out in the same manner as the previously mentioned step of removing the protective group and, if necessary, the ester residue following the sulfonation.

Furthermore, the compounds of the present invention can also be produced, for example, by reacting compound [A], for example a compound of the formula

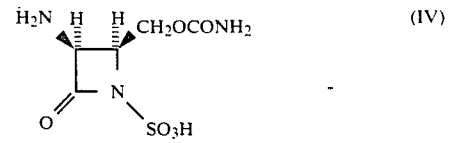
(IV)

or a salt or ester thereof with a compound of the formula

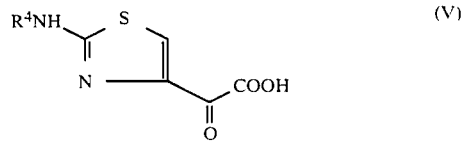
(V)

wherein R[4] is as defined above or a functional derivative thereof, subjecting the resulting compound of the formula

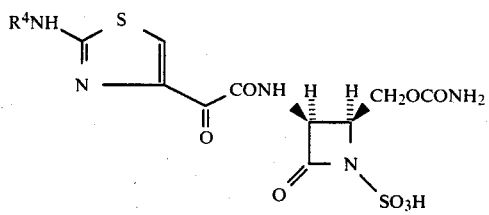

wherein R[4] is as defined above or a salt or ester thereof to dehydration condensation with a compound of the formula

wherein R[2] is as defined above, or a salt thereof, and removing the protective group and, if necessary, the ester residue. The reaction of compound [IV] with compound [V] can be carried out in the same manner as the reaction of compound [A] with carboxylic acid [II], and the dehydration condensation reaction of compound [VI] with compound [VII] can be carried out by the method substantially disclosed in Japanese Published unexamined patent application No. 125190/1977, for instance. The removal of the protective group and the ester residue is advantageously carried out in the same manner as mentioned above.

The final products of the present invention, namely compounds [III], obtained after the removal of the protective group and, if necessary, the ester residue are isolated and purified by per se known methods such as mentioned above. Compounds [III], having a sulfo group and a carboxyl group as well as an amino group, can generally form salts with bases and acids. Therefore, compounds [III] may be recovered in the form of salts, and the salts may be converted to free forms or different salts. Furthermore, compounds [III] obtained in the free form may be converted to salts. For converting salts of compounds [III] with bases to free forms, acids, for instance, may be used. The acid to used in a specific instance depends on the protective group species and other factors and includes, among others, such inorganic acids as hydrochloric, sulfuric and phosphoric acid and such organic acids as formic, acetic and p-toluenesulfonic acid, which are frequently used. Furthermore, acid-form ion exchange resins and the like are usable. In many cases, a hydrophilic organic solvent (e.g. acetone, tetrahydrofuran, methanol, ethanol, dioxane), water or a mixture thereof is used as the solvent. This procedure is generally carried out at room temperature but may be carried out with cooling or heating. The reaction time depends on the kind of acid, the kind of solvent and the temperature. In any case, however, a shorter reaction period is preferred. The thus-produced free forms of compounds [III] can be isolated by known methods such as mentioned above. Further, compounds [III] obtained in the form of free acids or salts may be converted to esters thereof by conventional methods.

Among the salts of the compound [III], a slat with a nontoxic cation, especially mono- or di-sodium salt is desirable. Di-sodium salt of the compound [III] can be recovered in crystalline form which is highly stable in storage and has high water solubility. Crystalline disodium salt of the compound [III] may be prepared, for example, by bringing non-crystalline di-sodium salt of the compound [III] into contact with water vapor until 0.2–0.7 times (by weight) of water to the salt has been absorbed, by condensing an aqueous solution of di-sodium salt of the compound [III] until the water content has become 0.2–0.7 times (by weight) to the salt, by adding an organic solvent to an aqueous solution of di-sodium salt of the compound [III], or the like. As an organic solvent, use is made of a water-miscible solvent, e.g., alcohols such as methanol, ethanol, n-propanol, isopropanol or n-butanol, ketones such as acetone or methyl ethyl ketone, nitriles such as acetonitrile or propionitrile, ethers such as diethylether, tetrahydrofuran or dioxane, or a mixture thereof, etc. The volume of solvent to be used is not limited as long as the purpose is attained. Usually, it is 1 to 100 parts per 1 part of the aqueous solution. The preparation of said crystals is normally conducted at the temperature in the range of 0°–40° C., preferably 10°–35° C., more preferably 15°–30° C. At a temperature lower than 0° C., the crystals grow too slowly, while at a higher temperature than 40° C., the starting material and/or the product decompose, and the recovery yield of crystallization decreases. The time required to form crystals varies according to the purity of the starting material, solvent, method for preparing crystals, temperature and so on. Generally, the preparation is accomplished within 3.0 minutes to 10 hours at a temperature of 15°–30° C. The thus-obtained crystals, after, if necessary, being washed with use of an organic solvent as mentioned above and-/or beeing subjected to dehydration, are isolated by filtration or centrifugation, for instance. The starting material, non-crystalline di-sodium salt of [III] may be obtained according to per se known methods. For example, to a solution or suspension of the compound [III] in water or mixture of water and organic solvent is added carbonic acid sodium salt such as sodium hydroxide, sodium carbonate or sodium hydrogen carbonate, aliphatic acid sodium salt such as sodium acetate, sodium propionate or sodium 2-ethylhexanate, aromatic carboxylic acid sodium salt such as sodium benzonate, in the proportion of two molecular equivalents or a slight excess to the compound [III] to give an aqueous solution of the d-sodium salt thereof. Lyophilization of the said aqueous solution may give the non-crystalline salt.

The starting compounds [I], [A] and [II] to be used in practicing the invention can be prepared, for example, by the methods shown below or modifications thereof.

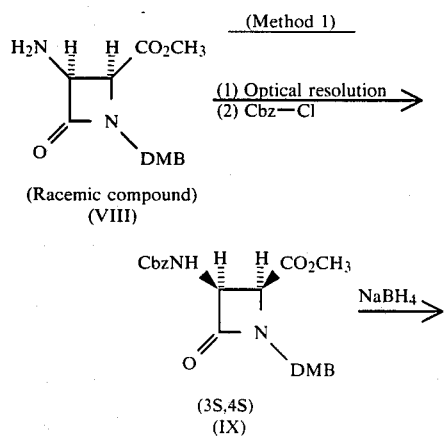

11
-continued

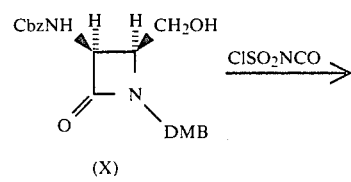
(X)

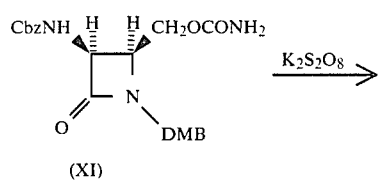
(XI)

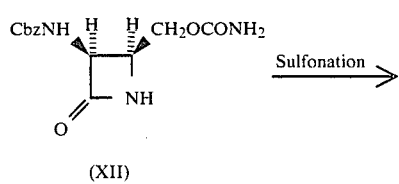
(XII)

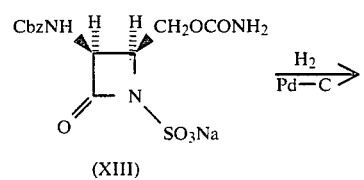
(XIII)

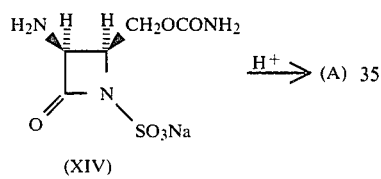
(XIV)

(Method 2)

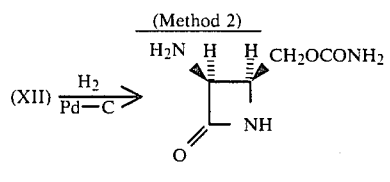
(XV)

(Method 3)

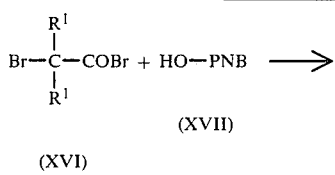
(XVI)  (XVII)

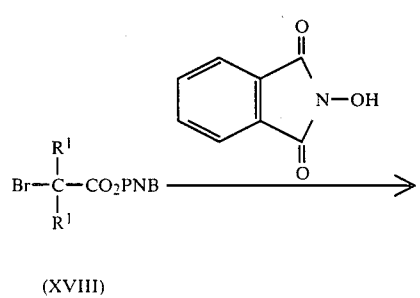
(XVIII)

12
-continued

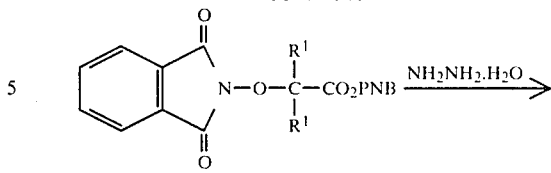
(XIX)

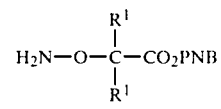
(XX)

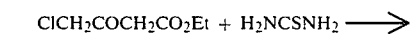
(XXI)   (XXII)

(XXIII)

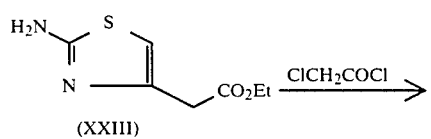
[XXIV]

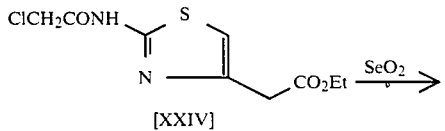
(XXV)

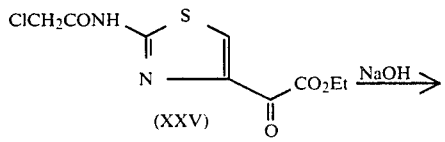
(XXVI)

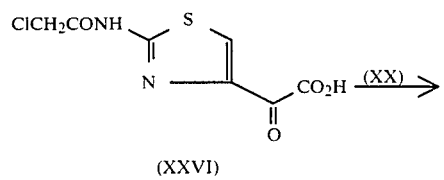
(II)

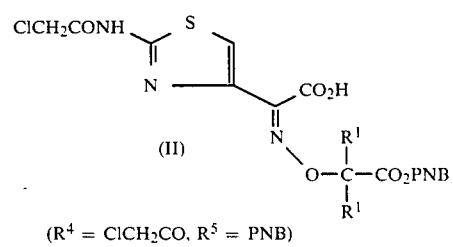

($R^4$ = ClCH$_2$CO, $R^5$ = PNB)

In the above formulas, DMB stands for 2,4-dimethoxybenzyl, Cbz for benzyloxycarbonyl, Et for ethyl, and PNB for p-nitrobenzyl, and $R^1$ is as defined above.

The starting material for method 1) shown above, namely cis-3-amino-4-methoxycarbonyl-1-(2,4-dimethoxybenzyl)-2-azetidinone [VIII], is a known compound described, for example, in the Journal of the American Chemical Society, vol. 99, page 2352 (1977) and can easily be prepared. Compound [II] can be prepared, for example, by method 3) shown above or a modification thereof. Detailed procedures are disclosed, for example, in Japanese Patent Applications Nos. 194311/1981 and 011965/1982.

The thus-obtained starting materials [I], [A] and [II] may be fed to the reaction step in accordance with the present invention either after isolation and purification by such conventional methods as mentioned above or in the form of a reaction mixture.

The starting compound [A] or a salt or ester thereof in this invention is one of compounds represented by the formula

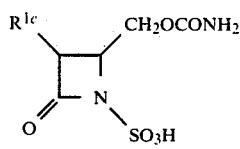

[A]' wherein $R^{1c}$ is an amino group which may optionally be protected, or salts or esters thereof which may be used to prepare 1-sulfo-2-oxazetidine compounds having carbamoyloxymethyl at 4-position. The salt or ester of the compound [A]' may include one as mentioned for the compound [III]. The amino group represented by $R^{1c}$ may be protected with such an amino-protecting group as mentioned above in the symbols $R^3$ and $R^4$, for example, an aromatic acyl, aliphatic acyl, esterified carboxyl, non-acyl amino-protecting group or the like. Among them, an $C_{7\text{-}13}$ aralkyloxycarbonyl (e.g. benzyloxycarbonyl) is preferable as the amino-protecting group of $R^{1c}$. The group $R^{1c}$ may have β-configuration to the azetidine ring. And, the compound [A]' may have the (3S,4S)-configuration. The compound [A]' or a salt or ester thereof can be produced by sulfonating a compound of the formula

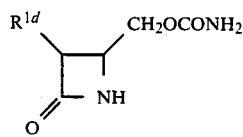

[A]"

wherein $R^{1d}$ is an amino group which may optionally be protected, or a salt or ester thereof, and if necessary, removing the protective gorup. The protective group for the amino group in $R^{1d}$ includes those exemplified hereinbefore for the group $R^{1c}$. The sulfonation reaction of the compound [A]" can be conducted in the same manner as the sulfonation reaction of the compound [I], and the removal of the protective group and the isolation of the compound [A]' can be accomplished by the conventional methods as mentioned above.

The following Test Example, Examples and Reference Examples will illustrate the aspect of the compounds [I]C' of the invention in more detail. However, they are given only for the purpose of illustration. They are by no means limitative of the present invention. Modifications may be made without departing from the scope of this aspect of the invention.

The column chromatographic elution procedure in any of the Examples and Reference Examples was carried out, unless otherwise stated, under observation by TLC (thin layer chromatography). In the TLC observation, Merck 60F$_{254}$ TLC plates and the same solvent systems as used in the column chromatographic elution were used with a UV detector for detection. The spot on the TLC plate was sprayed with 48% hydrobromic acid, heated for hydrolysis and then sprayed with the ninhydrin reagent. Upon reheating, the spot turned red to reddish violet. Using this phenomenon as an additional detection method, the eluate fractions containing the desired product were identified and collected. When two or more solvent systems were used as the developing solvents, unless otherwise stated, the solvent used first was for elution of the byproduct and the solvent used subsequently was for elution of the desired product. In the column chromatographic purification using Amberlite, water and aqueous ethanol solutions with gradually increasing ethanol concentrations were used in that order as the developing solvents unless otherwise stated in the relevant Examples and Reference Examples. Unless otherwise stated, anhydrous sodium sulfate was used as the desiccant in drying the solution containing the desired product.

"Amberlite" is a product of Rohm & Haas Co., U.S.A. and "Dowex" is a product of Dow Chemical Co. The NMR spectrometry was performed using an EM 390 (90 MHz) or T 60 (60 MHz) spectrometer with tetramethylsilane as the internal or external standard, and the total δ values were given in ppm. In the Examples and Reference Examples, the symbols have the meanings respectively given in the following:

s: singlet
d: doublet
q: quartet
ABq: AB type quartet
d.d: double doublet
m: multiplet
br.: broad
J: coupling constant
Hz: Hertz
mg: milligram(s)
g: gram(s)
ml: milliliter(s)
Ph: phenyl
MeOH: methanol
CHCl$_3$: chloroform
DMSO: dimethyl sulfoxide

TEST EXAMPLE

For the products respectively obtained in Example 2 and Example 4, the MIC values (mcg/ml) were determined by the method mentioned below and the results are shown below in the table.

Method

The MIC values for the test compounds were determined by the agar dilution method. Thus, 1.0 ml of each serially diluted aqueous solution of each test compound was poured into a petri dish. Then, 9.0 ml of Trypticase soy agar was added and mixed with the aqueous solution. A suspension of the test organism (about $10^6$ CFU/ml) was smeared onto the mixed agar plate and incubated overnight at 37° C. The lowest concentration of the test compound that completely inhibited the growth of the test organism was reported as the minimal inhibitory concentration (MIC).

Test organisms (1) Enterobacter cloacae IFO 12937
(2) Klebsiella pneumoniae TN 1711
(3) Pseudomonas aeruginosa GN 3407

Results

| Test compound | Test organism | | (mcg/ml) |
| --- | --- | --- | --- |
| | (1) | (2) | (3) |
| Example 2 | 0.05 | 0.05 | 1.56 |
| Example 4 | 0.39 | 0.1 | 6.25 |

Reference Example 1

To 600 ml of acetonitrile are added 23.54 g of cis-3-amino-4-methoxycarbonyl-1-(2,4-dimethoxybenzyl)-2-azetidinone and 16.17 g of di-(p-toluoyl)-D-tartaric acid monohydrate and the mixture is warmed for dissolution. The solution is filtered and allowed to cool. The crystalline precipitate is collected by filtration and washed with cooled acetonitrile to give 20.3 g of the salt, which is recrystallized from 300 ml of acetonitrile. The above procedure gives 16.3 g of the salt, melting at 165°-168° C.

$[\alpha]_D^{22} + 71.9°$ (c=0.985, MeOH)

The above salt is dissolved in a mixture of 100 ml of water and 200 ml of tetrahydrofuran and, following addition of 6.1 g of sodium hydrogen carbonate, 4.2 ml of carbobenzoxy chloride is added dropwise under ice-cooling and stirring. The mixture is stirred under ice-cooling for an hour and then at room temperature for an hour. The tetrahydrofuran is distilled off under reduced pressure at 30° C. or below (bath temperature). The residue is shaken with 400 ml of ethyl acetate and 200 ml of water and the aqueous layer is reextracted with 200 ml of ethyl acetate. The extracts are combined and washed twice with 2% aqueous sodium bicarbonate. The solution is further washed with aqueous sodium chloride, 1N hydrochloric acid and aqueous sodium chloride in that order and dried. The solvent is then distilled off under reduced pressure and 30 ml of ether is added to the residue. The crystalline precipitate is collected by filtration and dissolved in 50 ml of ethyl acetate with warming, and the solution is filtered. To the filtrate is added 50 ml of hexane and the mixture is allowed to cool. The resulting colorless crystals are recovered by filtration to give 6.45 g (37.5%) of (3S,4S)-cis-3-benzyloxycarboxamido-4-methoxycarbonyl-1-(2,4-dimethoxybenzyl)-2-azetidinone, melting at 120°-121° C.

$[\alpha]_D^{22} + 24.4°$ (c=1.08, CHCl$_3$)

IR$\nu_{max}^{Nujol}$ cm$^{-1}$: 3300, 1770, 1745, 1695.

Elemental analysis: $C_{22}H_{24}N_2O_7$

| | C (%) | H (%) | N (%) |
| --- | --- | --- | --- |
| Calcd.: | 61.67 | 5.65 | 6.54 |
| Found: | 61.50 | 5.59 | 6.37 |

Reference Example 2

In 300 ml of tetrahydrofuran is dissolved 12.8 g of (3S,4S)-cis-3-benzyloxycarboxamido-4-methoxycarbonyl-1-(2,4-dimethoxybenzyl)-2-azetidinone and, under ice-cooling and stirring, a solution of 2.8 g of sodium borohydride in 150 ml of ice water is added dropwise over 10 minutes. After completion of the addition, the mixture is stirred under ice-cooling for an hour and at room temperature for 3 hours. The tetrahydrofuran is distilled off under reduced pressure at 30° C. or below (bath temperature) and water is added to the residue. The mixture is filtered and the solid is washed with water and ethyl acetate to give 4.4 g of the crude crystalline product. The mother liquor and washings are combined and shaken. Thereafter the ethyl acetate layer is separated. The aqueous layer is reextracted with ethyl acetate. The ethyl acetate layers thus obtained are combined and washed with 1N hydrochloric acid and aqueous sodium chloride, dried over anhydrous sodium sulfate, and concentrated under reduced pressure. The residue and the crystals previously obtained are combined and recrystallized from ethyl acetate to give 9.1 g (76%) of (3S,4S)-cis-3-benzyloxycarboxamido-1-(2,4-dimethoxybenzyl)-4-hydroxymethyl-2-azetidinone as colorless crystals, melting at 137°-138° C.

$[\alpha]_D^{25} - 32.7°$ (c=1, CHCl$_3$)

IR$\nu_{max}^{Nujol}$ cm$^{-1}$: 3480, 3345, 1740, 1715, 1695.

NMR(CDCl$_3$)δ: 3.5-3.9(3H, C$_4$—H, C$_4$—CH$_2$), 3.78(3H, s, OCH$_3$), 3.79(3H, s, OCH$_3$), 4.35(2H, s, N$_1$—CH$_2$), 4.9-5.2(1H, m, C$_3$—H),

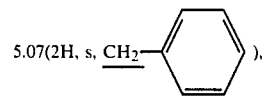

5.07(2H, s, CH$_2$—), 6.06(1H, d, J=10 Hz, C$_3$—NH), 6.3-6.6(2H, m, aromatic protons), 7.1-7.3(1H, m, aromatic protons),

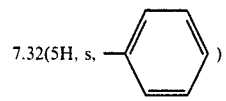

7.32(5H, s, —)

Elemental analysis: $C_{21}H_{24}N_2O_6$

| | C (%) | H (%) | N (%) |
| --- | --- | --- | --- |
| Calcd.: | 62.99 | 6.04 | 7.00 |
| Found: | 62.62 | 5.90 | 7.03 |

Reference Example 3

In 40 ml of methylene chloride is dissolved 2.0 g of (3S,4S)-cis-3-benzyloxycarboxamido-1-(2,4-dimethoxybenzyl)-4-hydroxymethyl-2-azetidinone and, under ice-cooling and stirring, 0.52 ml of chlorosulfonyl isocyanate is added. The mixture is stirred under ice-cooling for 30 minutes and, following addition of 0.35 ml of chlorosulfonyl isocyanate, the mixture is stirred for further 10 minutes. Then under ice-cooling, a solution of 1.26 g of sodium sulfite in 30 ml of water is added to the reaction mixture and the whole mixture is stirred at room temperature for an hour. The methylene chloride is distilled off under reduced pressure and the concentrate is extracted with chloroform. The extract is washed with aqueous sodium chloride and dried over anhydrous magnesium sulfate. The solvent is then distilled off under reduced pressure and ether is added to the residue. The mixture is filtered to give 2.46 g of the crude crystalline product, which is recrystallized from ethyl acetate-hexane to give 1.72 g (77.7%) of (3S,4S)-cis-3-benzyloxycarboxamido-4-carbamoyloxymethyl-1-(2,4-dimethoxybenzyl)-2-azetidinone as colorless crystals, melting at 179°-180° C.

$[\alpha]_D^{24.5} + 34.5°$ (c=0.8, DMSO).

IR$\nu_{max}^{KBr}$ cm$^{-1}$: 3410, 3300, 1760, 1710.

NMR(d$_6$-DMSO)δ: 3.74(3H, s, OCH$_3$), 3.76(3H, s, OCH$_3$), 3.7-4.3(3H, m, C$_4$—H, C$_4$—CH$_2$), 4.20(2H, ABq, J=15 Hz, N$_1$—CH$_2$), 4.92(1H, d.d, J=5, 10 Hz, C$_3$—H), 5.05(2H, s, CH$_2$ph), 7.35(5H, s, ph), 7.87(1H, d, J=10 Hz, C$_3$—NH).

Elemental analysis: C$_{22}$H$_{25}$N$_3$O$_7$

|  | C (%) | H (%) | N (%) |
|---|---|---|---|
| Calcd.: | 59.59 | 5.68 | 9.48 |
| Found: | 59.30 | 5.70 | 9.57 |

Reference Example 4

In a mixture of 36 ml of acetonitrile and 18 ml of water are suspended 1.60 g of (3S,4S)-cis-3-benzyloxycarboxamido-4-carbamoyloxymethyl-1-(2,4-dimethoxybenzyl)-2-azetidinone, 1.41 g of potassium persulfate and 0.85 g of dipotassium phosphate, and the suspension is stirred in an argon atmosphere at 95° C. (bath temperature) for 80 minutes. The acetonitrile is distilled off under reduced pressure and 10 ml of aqueous sodium chloride is added to the residue. The mixture is extracted with ethyl acetate-tetrahydrofuran and the extract is washed with 5% aqueous sodium bicarbonate and aqueous sodium chloride and dried over anhydrous magnesium sulfate. The solvent is then distilled off under reduced pressure and the solid residue is recrystallized from ethyl acetate to give 426 mg (40.3%) of (3S,4S)-cis-3-benzyloxycarboxamido-4-carbamoyloxymethyl-2-azetidinone as light-yellow crystals. The mother liquor is concentrated and purified by silica gel column chromatography [silica gel, 70 g; eluent: CHCl$_3$-MeOH-ethyl acetate (85:10:5)] to give 353 mg of colorless crystals as a further crop.

Total yield: 779 mg (73.6%)
m.p.: 191°–192° C.
[α]$_D^{25}$+60.6° (c=1, MeOH).
IRν$_{max}^{KBr}$ cm$^{-1}$: 3400, 3300, 1755(sh), 1745, 1695.
NMR(d$_6$-DMSO)δ: 3.70-4.25(3H, C$_4$—H, C$_4$—CH$_2$), 4.95(1H, d.d, J=5, 10 Hz, C$_3$—H), 5.05(2H, s, CH$_2$ph), 6.47(2H, br.s, CONH$_2$), 7.33(5H, s, ph), 7.92(1H, d, J=10 Hz, C$_3$—NH), 8.30(1H, br.s, N$_1$—H)

Elemental analysis: C$_{13}$H$_{15}$N$_3$O$_5$

|  | C (%) | H (%) | N (%) |
|---|---|---|---|
| Calcd.: | 53.23 | 5.15 | 14.32 |
| Found: | 52.83 | 5.02 | 14.26 |

Reference Example 5

In 10 ml of dioxane is dissolved 293 mg of (3S,4S)-cis-3-benzyloxycarboxamido-4-carbamoyloxymethyl-2-azetidinone and, following addition of 477 mg of sulfuric anhydridepyridine complex, the mixture is stirred at room temperature for 14 hours. The dioxane is distilled off under reduced pressure and the residue is stirred with 20 ml of water and 20 ml of Dowex 50W (Na) at room temperature for an hour. The resin is filtered off and the filtrate is concentrated under reduced pressure. The residue is chromatographed on an Amberlite XAD-2 column, elution being carried out with water, 5% ethanol and 10% ethanol in that order. The fractions containing the desired product are combined, concentrated under reduced pressure, and lyophilized to give 270 mg (64%) of sodium (3S,4S)-cis-3-benzyloxycarboxamido-4-carbamoyloxymethyl-2-azetidinone-1-sulfonate as a colorless powder.

[α]$_D^{25}$+29.4° (c=0.715, H$_2$O).
IRν$_{max}^{KBr}$ cm$^{-1}$: 3500, 3370, 3320, 1795, 1760, 1730, 1690.
NMR(d$_6$—DMSO)δ: 3.85-4.40(3H, C$_4$—H, C$_4$—CH$_2$), 4.92(1H, d.d, J=5, 10 Hz, C$_3$—H), 6.10-6.65(1H, CONH$_2$), 7.35(5H, s, ph), 7.98(1H, d, J=10 Hz, C$_3$—NH)

Elemental analysis: C$_{13}$H$_{14}$N$_3$NaO$_8$S.1½H$_2$O

|  | C (%) | H (%) | N (%) |
|---|---|---|---|
| Calcd.: | 36.97 | 4.06 | 9.95 |
| Found: | 37.24 | 4.13 | 10.02 |

Reference Example 6

In 50 ml of methanol is dissolved 674 mg of (3S,4S)-cis-3-benzyloxycarboxamido-4-carbamoyloxymethyl2-azetidinone and, following addition of 300 mg of 5% palladium-on-carbon, the mixture is stirred in a hydrogen atmosphere at room temperature for 30 minutes. The catalyst is then filtered off and the filtrate is concentrated under reduced pressure. The residue is dissolved in 20 ml of a 1:1 mixture of tetrahydrofuran and water and, under ice-cooling and stirring, 504 mg of sodium bicarbonate is added. Then, 1.62 g of 2-(2-chloroacetamido-4-thiazolyl)-(Z)-2-[1-methyl-1-(p-nitrobenzyloxycarbonyl)ethoxyimino]acetyl chloride hydrochloride is added and the mixture is stirred under ice-cooling for 30 minutes. To the reaction mixture is added 10 ml of aqueous sodium chloride and the mixture is extracted with ethyl acetate. The extract is washed with aqueous sodium bicarbonate and aqueous sodium chloride and dried over anhydrous magnesium sulfate. The solvent is then distilled off under reduced pressure and the residue is purified by silica gel column chromatography [silica gel, 60 g; eluent: ethyl acetate). The fractions containing the desired product are combined and the solvent is distilled off under reduced pressure. Ether is added to the residue and the colorless solid precipitate is collected by filtration to give 1.25 g (87%) of (3S,4S)-cis-3-[2-(2-chloroacetamido-4-thiazolyl)-2-(Z)-[1-methyl-1-(4-nitrobenzyloxycarbonyl)ethoxyiminoacetamido]-4-carbamoyloxymethyl-2-azetidinone, melting at 190°–195° C. (decompn.).

[α]$_D^{25}$+34.5° (c=0.145, MeOH).
IRν$_{max}^{KBr}$ cm$^{-1}$: 3450, 3300, 1753, 1740 (sh), 1690, 1660
NMR(d$_6$-DMSO)δ: 1.51(3H, s, CH$_3$), 1.53(3H, s, CH$_3$), 3.8-4.4(3H, C$_4$—H, C$_4$—CH$_2$), 4.37(2H, s, ClCH$_2$), 5.2-5.45(3H, C$_3$—H, CH$_2$ph), 6.53(2H, br.s, CONH$_2$), 7.38(1H, s, proton at position 5 of the thiazole ring), 7.62(2H, d, J=8 Hz, aromatic protons), 8.07(2H, d, J=8 Hz, aromatic protons), 8.50(1H, br.s, N$_1$—H), 9.23(1H, d, J=9 Hz, C$_3$—NH).

EXAMPLE 1

In a mixture of 10 ml of water and 10 ml of tetrahydrofuran is dissolved 422 mg of sodium (3S,4S)-cis-3-benzyloxycarboxamido-4-carbamoyloxymethyl-2-azetidinone-1-sulfonate and, following addition of 422 mg of 10% palladium-on-carbon, the mixture is stirred in a hydrogen atmosphere at room temperature for an hour. The catalyst is then filtered off and washed with 30 ml of a 1:1 mixture of water and tetrahydrofuran. The filtrate and washings are combined and, under ice-cooling and stirring, 202 mg of sodium bicarbonate is added. Then, 614 mg of 2-(2-chloroacetamido-4-thiazolyl)-2-(Z)-(p-nitrobenzyloxycarbonylmethoxyimino)acetyl chloride hydrochloride is added and the mixture is stirred under ice-cooling for 30 minutes, then adjusted to pH 5 with 1N hydrochloric acid, and concentrated to 30 ml under reduced pressure. To the residue is added 10 ml of tetrahydrofuran and, following addition of 129 mg of sodium N-methyldithiocarbamate, the mixture is stirred at room temperature. After 40 and 80 minutes, 129 mg portions of sodium N-methyldithiocarbamate are added respectively. Stirring is thus continued for 2 hours in total. The tetrahydrofuran is then distilled off under reduced pressure and the residual aqueous solution is washed with ether and concentrated again under reduced pressure. The concentrate is chromatographed on a column of Amberlite XAD-2 (200 ml), elution being carried out with water, 5% ethanol, 10% ethanol, 15% ethanol and 20% ethanol in that order. The fractions containing the desired product are combined, concentrated under reduced pressure and lyophilized to give 500 mg (76%) of sodium (3S,4S)-cis-3-[2-(2-amino-4thiazolyl)-2-(Z)-(p-nitrobenzyloxycarbonylmethoxyimino)acetamido]-4-carbamoyloxymethyl-2-azetidinone-1-sulfonate as a light-yellow powder.

$[\alpha]_D^{26} +10.1°$ (c=1, $H_2O$).

IR$\nu_{max}^{KBr}$ cm$^{-1}$: 1760, 1720(br.sh), 1670

NMR(d$_6$—DMSO)δ: 3.9-4.4(3H, C$_4$—H, C$_4$—CH$_2$), 4.78(2H, s, OCH$_2$—COOCH$_2$), 5.28(1H, d.d, J=4.5, 10 Hz, C$_3$—H), 5.35(2H, s, OCH$_2$—COOCH$_2$), 6.45(2H, br.s, CONH$_2$), 6.76(1H, s, proton at position 5 of the thiazole ring), 7.18(2H, br.s, amino at position 2 of the thiazole ring), 7.68(2H, d, J=8 Hz, aromatic protons), 8.19(2H, d, J=8 Hz, aromatic protons), 9.18(1H, d, J=10 Hz, C$_3$—NH).

Elemental analysis: $C_{19}H_{18}N_7NaO_{12}S_2 \cdot 2H_2O$

|  | C (%) | H (%) | N (%) |
|---|---|---|---|
| Calcd.: | 34.60 | 3.36 | 14.87 |
| Found: | 34.44 | 3.10 | 14.82 |

EXAMPLE 2

In 20 ml of water is dissolved 350 mg of sodium (3S,4S)-cis-3-[2-(2-amino-4-thiazolyl)-2-(Z)-(p-nitrobenzyloxycarbonylmethoxyimino)acetamido]-4-carbamoyloxymethyl-2-azetidinone-1-sulfonate and, following addition of 350 mg of 10% palladium-on-carbon, the mixture is stirred in a hydrogen atmosphere at room temperature for an hour. The catalyst is then filtered off and washed with water. The filtrate and washings are combined and stirred with 40 ml of Dowex 50W (H) under ice-cooling for an hour. The resin is filtered off and washed with a mixture of water and acetone. The filtrate and washings are combined and concentrated under reduced pressure. The residue is chromatographed on a column of Amberlite XAD-2 (150 ml), elution being carried out with water and 5% ethanol in that order. The fractions containing the desired product are combined, concentrated under reduced pressure and lyophilized to give 164 mg (61%) of (3S,4S)-cis-3-[2-(2-amino-4-thiazolyl)-2-(Z)-carboxymethoxyimino)acetamido]-4-carbamoyloxymethyl-2-azetidinone-1-sulfonic acid as a colorless powder.

$[\alpha]_D^{26} -45°$ (c=1, DMSO) IR$\nu_{max}^{KBr}$ cm$^{-1}$: 1760, 1715, 1670, 1640 NMR(d$_6$—DMSO)δ: 3.9-4.4(3H, C$_4$—H, C$_4$—CH$_2$), 4.66(2H, s, NO—CH$_2$), 5.28(1H, d.d, J=4.5, 10 Hz, C$_3$—H), 6.92(1H, s, proton at position 5 of the thiazole nuclear), 9.33(1H, d, J=10 Hz, C$_3$—NH)

EXAMPLE 3

In 5 ml of N,N-dimethylformamide is dissolved 1.13 g of (3S,4S)-cis-3-[2-(2-chloroacetamido-4-thiazolyl)-2-(Z)-[1-methyl-1-(4-nitrobenzyloxycarbonyl)ethoxyimino]acetamido]-4-carbamoyloxymethyl-2-azetidinone and, under cooling at −78° C., 2.08 ml of sulfuric anhydride-N,N-dimethylformamide complex solution (1.56M) is added. The mixture is stirred under ice-cooling for 3 hours and, under cooling at −78° C., 0.23 ml of the same complex solution as above is further added. The whole mixture is stirred under ice-cooling for an additional hour and, upon addition of 0.29 ml of pyridine and then 100 ml of ether, a syrupy precipitate separates out. The upper ether layer is discarded and the syrupy product is dissolved in water and stirred with 30 ml of Dowex 50W (Na) at room temperature for an hour. The resin is then filtered off and the filtrate is concentrated to about 30 ml under reduced pressure. To the residue is added 232 mg of sodium N-methyldithiocarbamate and the mixture is stirred at room temperature. After 1 and 2 hours, 232 mg portions of sodium N-methyldithiocarbamate are added respectively. Stirring is thus continued for 3 hours in total. The reaction mixture is washed with ether and concentrated under reduced pressure. The residue is chromatographed on a column of Amberlite XAD-2 (180 ml), elution being carried out with water, 5% ethanol, 10% ethanol, 15% ethanol and 20% ethanol in that order. The fractions containing the desired product are combined, concentrated under reduced pressure and lyophilized to give 579 mg (46.4%) of sodium (3S,4S)-cis-3-[2-(2-amino-4-thiazolyl)-2-(Z)-[1-methyl-1-(4-nitrobenzyloxycarbonyl)ethoxyimino]acetamido]-4-carbamoyloxymethyl-2-azetidinone-1-sulfonate as a light-yellow powder.

$[\alpha]_D^{25} +6.5°$ (c=1, $H_2O$).

IR$\nu_{max}^{KBr}$ cm$^{-1}$: 1760, 1725, 1670.

NMR(d$_6$—DMSO)δ: 1.47(6H, s, 2×CH$_3$), 3.95-4.35(3H, C$_4$—H, C$_4$—CH$_2$), 5.20-5.45(3H, C$_3$—H, OCH$_2$), 6.43(2H, br.s, CONH$_2$), 6.68(1H, s, proton at position 5 of the thiazole ring), 7.23(2H, br.s, amino at position 2 of the thiazole ring), 7.63(2H, d, J=8 Hz, aromatic protons), 8.11(2H, d, J=8 Hz, aromatic protons), 9.00(1H, d, J=9 Hz, C$_3$—NH)

Elemental analysis: $C_{21}H_{22}N_7NaO_{12}S_2 \cdot 2\frac{1}{2}H_2O$

|  | C (%) | H (%) | N (%) |
|---|---|---|---|
| Calcd.: | 36.21 | 3.91 | 14.08 |
| Found: | 36.36 | 3.73 | 14.05 |

EXAMPLE 4

In 17 ml of water is dissolved 344 mg of sodium (3S,4S)-cis-3-[2-(2-amino-4-thiazolyl)-2-(Z)-[1-methyl-1-(4-nitrobenzyloxycarbonyl)ethoxyimino]acetamido]-4-carbamoyloxymethyl-2-azetidinone-1-sulfonate and, following addition of 344 mg of 10% palladium-on-carbon, the mixture is stirred in a hydrogen atmosphere at room temperature for 50 minutes. The catalyst is then filtered off and washed with water. The filtrate and washings are combined, 42 mg of sodium bicarbonate is added under ice-cooling and the mixture is washed with ethyl acetate. The aqueous solution is stirred with 40 ml of Dowex 50W (H) under ice-cooling for an hour. The resin is filtered off and the filtrate is concentrated under reduced pressure. The residue is chromatographed on a column of Amberlite XAD-2 (150 ml), elution being carried out with water, 5% ethanol and 10% ethanol in that order. The fractions containing the desired product are combined, concentrated under reduced pressure and lyophilized to give 185 mg (70%) of (3S,4S)-cis-3-[2-(2-amino-4-thiazolyl)-2-(Z)-(1-carboxy-1-methylethoxyimino)acetamido]-4-carbamoyloxymethyl-2-azetidinone-1-sulfonic acid as a colorless powder.

$[\alpha]_D^{25} + 34.3°$ (c−1, $H_2O$).

$IR\nu_{max}^{KBr}$ $cm^{-1}$: 1760, 1715(br.), 1635.

NMR($d_6$—DMSO)δ: 1.46(6H, s, 2×$CH_3$), 3.95–4.4(3H, $C_4$—H, $C_4$—$CH_2$), 5.31(1H, d.d, J=4.5, 10 Hz, $C_3$—H), 6.91(1H, s, proton at position 5 of the thiazole ring), 9.14(1H, d, J=10 Hz, $C_3$—NH).

Elemental analysis: $C_{14}H_{18}N_6O_{10}S_2·2H_2O$

|  | C (%) | H (%) | N (%) |
| --- | --- | --- | --- |
| Calcd.: | 31.70 | 4.18 | 15.84 |
| Found: | 31.93 | 4.39 | 15.56 |

EXAMPLE 5

A wet cake comprising 169 g of (3S,4S)-cis-3-[2-(2-amino-4-thiazolyl)-(Z)-2-carboxymethoxyiminoacetamido]-4-carbamoyloxymethyl-2-azetidinone-1-sulfonic acid and 337 g of water, and 60.3 g of sodium hydrogen carbonate were added in alternate portions to 200 ml of water with constant stirring at the pH of ≦5 and the temperature of 0° to 5° C. The resulting solution was stirred under reduced pressure to remove the carbon dioxide gas. Then, 0.6 g of sodium hydrogen carbonate was further added in several portions and a further amount of carbon dioxide gas was removed under reduced pressure to give a solution of pH 5.9. To this solution was added 8.4 g of activated carbon and after 5 minutes' stirring at 5° C., the carbon was separated and washed with 140 ml of water. The filtrate and washings were combined, and 2.70 l of ethanol was added. The mixture was stirred at 25° C. Starting 40 minutes after crystals began to separate out, 2.04 l of ethanol was added dropwise over 20 minutes, the whole mixture was stirred at 25°±2° C. for 50 minutes, and then the crystals were recovered by filtration, washed with a mixture of 420 ml of ethanol and 60 ml of water and dried in vacuo at 25°-30° C. The above procedure provided 181 g crystals of (3S,4S)-cis-3-[2-(2-amino-4-thiazolyl)-(Z)-2-carboxymethoxyiminoacetamido]-4-carbamoyloxymethyl-2-azetidinone-1-sulfonic acid disodium salt.

$^1$H-NMR ($D_2O$, δ ppm): 4.2–4.8 (m, CHCH$_2$OCO, OCH$_2$COONa) 5.6 (1H, d, J=5 Hz, O=C—$\overline{\text{CH}}$), 7.0 (1$\overline{\text{H}}$, s, H-thiazole)

Elemental analysis: Calcd. for $C_{12}H_{12}N_6O_{10}S_2·Na_2·0.46H_2O$: C, 27.79%; H, 2.51%, N, 16.19%; S, 12.35%; Na, 8.9%, Found: C, 27.91%, H, 2.62%, N, 16.37%; S, 12.22%; Na, 8.2%.

The powder X-ray diffraction pattern of this product (FIG. 1; CuKα, 40 KV, 45 mA) shows the crystallinity thereof.

EXAMPLE 6

A wet cake containing 7.07 g of (3S,4S)-cis-3-[2-(2-amino-4-thiazolyl)-(Z)-2-carboxymethoxyiminoacetamido]-4-carbamoyloxymethyl-2-azetidinone-1-sulfonic acid and 20 g of water and 4.56 g of sodium acetate trihydrate were added in alternate portions to 10 ml of water with constant stirring. To the resulting solution was added 0.14 g of activated carbon and after 5 minutes' stirring at 5° C., the carbon was separated and washed with 5 ml of water. The filtrate and washings were combined and 112 ml of ethanol was added. The mixture was stirred at 25° C. Starting 30 minutes after crystals began to separate out, 84 ml of ethanol was added dropwise over 15 minutes. The mixture was stirred for an hour, after which the crystals were recovered by filtration, washed with a mixture of 28 ml of ethanol and 4 ml of water and dried in vacuo. The above procedure provided 7.40 g of crystals of (3S,4S)-cis-3-[2-(2-amino-4-thiazolyl)-(Z)-2-carboxymethoxyiminoacetamido]-3-carbamoyloxymethyl-2-azetidinone-1-sulfonic acid disodium salt.

The NMR spectrum and the powder X-ray diffraction pattern of this product were in good agreement with those of the compound obtained in Example 5.

Elemental analysis: Calcd. for $C_{12}H_{12}N_6O_{10}S_2·Na_2·0.49H_2O$: C, 27.76%; H, 2.52%; N, 16.19%, S, 12.35%, Na, 8.9%, Found: C, 27.94%, H, 2.80%, N, 16.52%, S, 12.59%, Na, 8.7%.

EXAMPLE 7

(1) After 191.2 g (1.25 mol) of p-nitrobenzyl alcohol is dissolved in 250 ml of methylene chloride, 98.8 g of pyridine is added, and the mixture is cooled to −5° to 0° C. A solution of 193.75 g (1.25 mol) of ε-chloroacetoacetyl chloride (γ-CAC) in 431 ml of methylene chloride is added at the same temperature over an hour and, after completion of the addition, the mixture is stirred for 30 minutes. The resulting pyridine hydrochloride is filtered off. The filtrate and washings are combined and washed with two 2 l-portions of water. The organic layer is dried over sodium sulfate and the solvent is then distilled off to give 354 g of p-nitrobenzyl γ-chloroacetoacetate as an oil.

NMR (CDCl$_3$)δ: 3.80 (2H, s, COCH$_2$COO), 4.30 (2H, s, ClCH$_2$CO), 5.27 (2H, s, COOCH$_2\overline{\text{C}}_6$H$_4$), 7.50 (2H, d, J=8 $\overline{\text{Hz}}$, aromatic protons) 8.15 $\overline{\text{(2H}}$, d, J=8 Hz, aromatic protons).

(2) In 100 ml of acetic acid is dissolved 50 g (0.184 mol, uncorrected for purity) of the crude p-nitrobenzyl γ-chloroacetoacetate obtained in 1), and the solution is cooled to 5° C. or lower, and a solution of 12.7 g (0.184 mol) of sodium nitrite in 50 ml of water is added dropwise thereto at 5° C. or lower over a period of an hour. After completion of the addition, the mixture is stirred for 30 minutes and poured into 600 ml of ice water and extracted with 300-ml and 200-ml portions of ethyl acetate. The organic layers are combined and washed with saturated aqueous sodium chloride, dried over sodium sulfate and concentrated to dryness to give 54.0 g of p-nitrobenzyl α-hydroxyimino-γ-chloroacetoacetate as an oil.

NMR (CDCl$_3$)δ: 4.60 (2H, s, ClCH$_2$CO), 5.40 (2H, s, COOCH$_2$C$_6$H$_4$), 7.52 (2H, d, J=8 $\overline{\text{Hz}}$, aromatic protons), 8.12 (2H, d, J=8 Hz, aromatic protons).

(3) In a mixture of 225 ml of ethanol and 225 ml of water is dissolved 50 g (0.167 mol, uncorrected for purity) of the crude p-nitrobenzyl α-hydroxyimino γ-chloroacetoacetate obtained in 2), and 12.7 g (0.167 mol) of thiourea and 22.7 g (0.167 mol) of sodium acetate trihydrate are added. The reaction is allowed to proceed at room temperature for 6 hours. On addition of 900 ml of water, an oily product separates out. After 30 minutes' stirring, the oil is separated and 400 ml of ethyl acetate is added, whereupon crystals separate out. After cooling, the crystals are recovered by filtration, washed with a small amount of ether and dried to give 14.9 g of p-nitrobenzyl 2-(2-amino-4-thiazolyl)-2-hydroxyiminoacetate.

IR$\nu$(KBr) cm$^{-1}$: 3400, 3300, 3180, 3100, 1730, 1615, 1525, 1360.

NMR (d$_6$—DMSO)$\delta$: 5.57 (2H, s, COOCH$_2$C$_6$H$_4$), 6.95 (1H, s, thiazole-5H), 7.22 (2H, s, NH$_2$—), 7.80 (2H, d, J=8 Hz, aromatic protons), 8.35 (2H, d, J=8 Hz, aromatic protons).

(4) In 60 ml of acetonitrile is suspended 3.0 g (9.3 mmol) of p-nitrobenzyl 2-(2-amino-4-thiazolyl)-2-hydroxyiminoacetate as obtained in (3), and 2.0 g (1.03 mmol) of t-butyl bromoacetate, 0.3 ml of water and 5.14 g (37 mmol) of anhydrous potassium carbonate are added in that order. The mixture is stirred at 40°–41° C. for an hour. After completion of the reaction, the mixture is poured into 300 ml of water and extracted with 300 ml of ethyl acetate. The organic layer is washed with three 300-ml portions of 5% aqueous sodium chloride, dried over sodium sulfate and concentrated to about 30 ml under reduced pressure. To the concentrate is added 100 ml of ether, and the mixture is cooled to 5° C. or lower. The resulting crystalline precipitate is collected by filtration, washed with a small amount of ether, and dried in vacuo to give 2.7 g of p-nitrobenzyl (Z)-2-(2-amino-4-thiazolyl)-2-(t-butoxycarbonylmethoxyimino)acetate.

IR$\nu$(KBr) cm$^{-1}$: 3420, 3250, 3150, 1735, 1620, 1528, 1390, 1360.

NMR (d$_6$—DMSO)$\delta$: 1.47 (9H, s, CH$_3\times$3), 4.61 (2H, s, NOCH$_2$COO), 5.50 (2H, z, COOCH$_2$C$_6$H$_4$), 6.92 (1H, s, thiazole-5H), 7.24 (2H, br. NH$_2$—), 7.72 (2H, d, J=8 Hz, aromatic protons), 8.26 (2H, d, J=8 Hz, aromatic protons).

(5) In 1.2 l of tetrahydrofuran is dissolved 20 g (45.9 mmol) of p-nitrobenzyl (Z)-2-(2-amino-4-thiazolyl)-2-(t-butoxycarbonylmethoxyimino)acetate and, after addition of 20 g of 10% palladium-on-carbon, hydrogen gas is bubbled into the solution. After completion of the reaction, the catalyst is filtered off, and the filtrate is poured into 300 ml of water. The mixture is adjusted to about pH 8 with 5% aqueous sodium bicarbonate and washed with three 200-ml portions of ethyl acetate. The aqueous layer is adjusted to pH about 2 with 10% HCl and cooled to 5° C. or lower. The resulting crystalline precipitate is collected by filtration, washed with water and dried under reduced pressure to give 11.1 g of (Z)-2-(2-amino-4-thiazolyl)-2-(t-butoxycarbonylmethoxyimino)acetic acid.

IR$\nu$(KBr) cm$^{-1}$: 3310, 3125, 1740, 1640, 1605, 1585.

NMR (d$_6$—DMSO)$\delta$: 1.48 (9H, s, CH$_3\times$3), 4.58 (2H, s, OCH$_2$COO), 6.86 (1H, s, thiazole-5H).

(6) In 140 ml of dry acetonitrile is suspended 5.42 g (18 mmol) of (Z)-2-(2-amino-4-thiazolyl)-2-(t-butoxycarbonylmethoxyimino)acetic acid, 2.96 ml (27 mmol) of N-methyl morpholine and then 7.2 g (21.6 mmol) of bis-benzothiazol-2-yl disulfide are added, and the mixture is cooled to 0° C. A solution of 5.38 ml (31.4 mmol) of triethyl phosphite in 35 ml of dry acetonitrile is added dropwise over 4.5 hours and the mixture is stirred at the same temperature for 30 minutes and then cooled to −10° C. The resulting crystalline precipitate is collected by filtration, washed with a small amount of acetonitrile and dried under reduced pressure to give 5.1 g of (Z)-2-(2-amino-4-thiazolyl)-2-(t-butoxycarbonylmethoxyimino)acetic acid 2-benzothiazolylthiol ester.

IR$\nu$(KBr) cm$^{-1}$: 3400, 3120, 1738, 1710, 1620, 1540, 1450, 1415, 1370.

NMR (d$_6$—DMSO)$\delta$: 1.50 (9H, s, CH$_3\times$3), 4.78 (2H, s, NOCH$_2$COO), 7.10 (1H, s, thiazole-5H), 7.4–7.65 (2H, m, aromatic protons), 8.0–8.3 (2H, m, aromatic protons.

EXAMPLE 8

A flask of 1.0 l capacity is charged with 0.06 kg (0.2508 mol) of (3S,4S)-3-amino-4-carbamoyloxymethyl-2-azetidinone-1-sulfonic acid and 0.9 l of methylene chloride to make a suspention, 0.070 l (0.2508×2 mol) of triethylamine and then 0.124 kg (0.2508×1.1 mol) of (Z)-2-(2-amino-4-thiazolyl-2-t-butoxycarbonylmethoxyimino)acetic acid 2-benzothiazolylthio ester are added to the suspension under stirring at 10°–20° C., and the mixture is stirred at 25°–27° C. for 4 hours. The insoluble matter is filtered off and the filtrate is further stirred for about an hour and extracted with 0.9 l of water. The aqueous layer is washed with 0.19 l of methylene chloride, 0.38 l of ethyl acetate and 0.19 l of methylene chloride in that order. After degassing, 0.45 l of concentrated hydrochloric acid is added and the mixture is stirred at 25° C. for about 2 hours. To the resulting slurry is added 0.9 l of water and the mixture is stirred to about 25° C. for about 2 hours and then allowed to stand at 0°–2° C. overnight. The resulting precipitates are collected by filtration and washed with about 0.6 l of cold water to give about 0.27 kg of (3S,4S)-3-[2-(2-amino-4-thiazolyl)-(Z)-2-(carboxymethoxyimino)acetamido]-4-carbamoyloxymethyl-2-azetidinone-1-sulfonic acid as wet crystals.

EXAMPLE 9

1.62 g of (3S,4S)-3-amino-4-carbamoyloxymethyl-2-oxo-1-azetidine-sulfonic acid-sodium salt in 180 ml of acetone-water (2:1) are stirred with 3.87 g of (Z)-2-(2-amino-4-thiazolyl)-2-[[1-(t-butoxycarbonyl)-1-methylethoxy]imino]-acetic acid 2-benzthiazolyl-thioester at room temperature for 15 hours. After removal of the acetone in vacuo and the addition of 50 ml of water, crystals are obtained which are washed with water. The mother liquor is evaporated under reduced pressure at 37° C. and chromatographed (MCI Gel, water as eluting agent). After lyophilization (3S,4S)-3-[(2-amino-4-thiazolyl)-2-(Z)-[[1-(t-butoxycarbonyl)-1-methylethoxy]imino]-acetamido]-4-carbamoyloxymethyl-2-oxo-1-azetidinesulfonic acid-sodium salt is obtained.

IR (KBr) cm$^{-1}$: 1766, 1723, 1683, 1617, 1531, 1458, 1369.

NMR (d$_6$DMSO, $\delta$ ppm): 1.35(15H, s), 4.0–4.15(3H, H$_4$ and CH$_2$—OCONH$_2$), 5.25(1H, dd, H$_3$), 6.5(2H, broad, CONH$_2$), 6.7(1H, s, H-thiazol), 7.25(2H, s, NH$_2$), 8.9(1H, d, CO—NH).

The above 2-benzothiazoyl-thioester can be manufactured as follows:

43 g of 2-(2-amino-4-thiazolyl)-2-(Z)-hydroxyiminoacetic acid-ethylester in 1.2 l of dimethylformamide are treated under nitrogen with 89.2 g of 2-bromo-2-methyl-propionic acid-t-butylester and 110.6 g of powdered potassium carbonate. After stirring for 12 hours at 45° C. the reaction mixture is cooled to room temperature, 4 l of water are added, and the mixture is extracted with 3.5 l of ethyl acetate. After washing of the organic extract with water, drying with magnesium sulfate and evaporation to dryness 2-(2-amino-4-thiazolyl)-2-[[(Z)-1-(t-butoxycarbonyl)-1-methylethoxy]imino]-acetic acid -ethyl ester is obtained, which after recrystallization from ether melts at 172° C.

240 g of the so obtained ethyl ester are stirred for 12 hours at 50° C. in 1.3 l of methanol and 1.34 l of 1N aqueous caustic soda solution. After evaporation of the methanol, washing of the aqueous phase with ethyl acetate and the addition of 1.34 l of 1N aqueous hydrochloric acid the product crystallizes out. The crystals are filtered off at 0° C., washed successively with water, acetonitrile and ether and dried in vacuo at 40° C. After stirring for 2 hours in acetonitrile (so as to remove crystal water), filtration and drying in vacuo at 40° C. 2-(2-amino-4-thiazolyl)-2-[[(Z)-1-(t-butoxycarbonyl)-1-methylethoxy]imino]-acetic acid, melting at 178°–179° C., is obtained.

28.8 g of the so obtained acetic acid derivative are dispersed in 360 ml of acetonitrile. With stirring 14.4 ml of N-methylmorpholine are added, and after 10 minutes 34.6 g of 2,2-dithio-bis-benzothiazole. The suspension is cooled to 0° C., 20.2 mml of triethylphosphite are slowly added within the course of 2 hours, and the suspension is stirred for another 12 hours at 0° C. The product is filtered off, washed successively with cold acetonitrile, isopropyl ether and petroleum ether and dried at room temperature in vacuo. 2-(2-Amino-4-thiazolyl)-2-[[(Z)-1-(t-butoxycarbonyl)-1-methylethoxy]imino]acetic acid-2-benzothiazole-thioester, melting at 139°–140° C., is obtained.

EXAMPLE 10

2.28 g of (3S,4S)-3-[(2-amino-4-thiazolyl)-2-(Z)-[[1-(t-butoxycarbonyl)-1-methylethoxy]imino]acetamido]-4-carbamoyloxymethyl-2-oxo-1-azetidinesulfonic acid-sodium salt are stirred at 0° C. with 5 ml of trifluoroacetic acid. After additional stirring at room temperature for 30 minutes the excess trifluoroacetic acid is removed in vacuo and the remaining oil treated with 100 ml of ether. The resulting crystals are filtered off, washed with ether and dried in vacuo. The product is purified by reverse phase chromatography and lyophilized. (3S,4S)-3-[(Z)-2-(2-Amino-4-thiazolyl)-2-[[1-carboxy-1-methylethoxy]imino]acetamido]-4-carbamoyloxymethyl-2-oxo-1-azetidinesulfonic acid is obtained; $[\alpha]_D = +35.7°$ (c=0.3 in water).

Elementary analysis: Calcd. for $C_{14}H_{18}N_6O_{10}S_2$: C, 34.01; H, 3.67; N, 17.00. Found: C, 34.52; H, 3.72; N, 16.63.

IR (KBr) cm$^{-1}$: 1764, 1722, 1680, 1637.

NMR (d$_6$DMSO, $\alpha$ ppm): 1.50(6H, s, 2×CH$_3$), 4.00–4.20(3H, CH—CH$_2$), 5.35(1H, dd, 4, 5 and 9 Hz, H$_3$), 6.50(3H, broad, NH$_3$+ or COH, CONH$_2$), 6.90(1H, s, thiazole-5H), 9.15(1H, d, 9 Hz, CONH).

EXAMPLE 11

In a manner analogous to Example 9 reaction of 2-(2-amino-4-thiazolyl)-2-[[(Z)-(p-nitrobenzyloxycarbonyl)-methoxy]imino]acetic acid-2-benzothiazolyl-thioester with (3S,4S)-3-amino-4-carbamoyloxymethyl-2-oxo-1-azetidine sulfonic acid-sodium salt yields (3S,4S)-3-[(Z)-2-(2-amino-4-thiazolyl)-2-[[(p-nitrobenzyloxycarbonyl)-methoxyimino]acetamido]-4-carbamoyloxymethyl-2-oxo-1-azetidine-sulfonic acid-sodium salt.

Elementary analysis: Calcd. for $C_{19}H_{18}N_7O_{12}S_2Na$: C, 36.60; H, 2.91; N, 15.73; S, 10.28, Found: C, 37.00; H, 2.88; N, 15.74; S, 10.45.

IR (KBr) cm$^{-1}$: 3353, 1761, 1729, 1524, 1348.

NMR (d$_6$DMSO, $\delta$ ppm): 4.0–4.2(3H, m, CH—CH$_2$), 4.7(2H, s, O—CH$_2$), 5.30(1H, dd, NH—CH—), 5.32(2H, s, O—CH$_2$), 6.70(2H, broad, NH$_2$), 6.9(1H, s, S—CH—), 7.10(2H, broad, NH$_2$), 7.70 and 8.2(2×2H, 2d, 2×3 Hz, Ar), 9.15(1H, d, 9 Hz, NHCO).

The 2-benzothiazolyl-thioester used above can be manufactured as follows:

6.1 g of 2-(2-amino-4-thiazolyl)-2-(Z)-hydroxyiminoacetic acid-t-butylester in 250 ml of dry acetonitrile are stirred at room temperature with 13.7 g of bromoacetic acid-4-nitrobenzylester and 12.9 ml of N-ethyldiisopropylamine. After 5 minutes 7.5 g of sodium iodide are added, and the reaction mixture is stirred for an additional 3½ hours in an argon atmosphere at room temperature. After evaporation of the solvent, dilution with 500 ml of ethyl acetate, washing with water, drying over sodium sulfate and evaporation to dryness 2-(2-amino-4-thiazolyl)-2-[[(p-nitrobenzyloxycarbonyl)-methoxy]imino]acetic acid-t-butylester is obtained, which after crystallization from ethyl acetate-n-hexane melts at 146.8° C. (dec.).

5.0 g of the so obtained t-butylester in 86 ml of acetic acid are stirred with 5.2 ml of boron trifluoride etherate. After stirring for 5 hours at room temperature and mixing with 260 ml of water the precipitate obtained is filtered off and dried at 40° C. in vacuo. 2-(2-Amino-4-thiazolyl)-2-[[(Z)-(p-nitrobenzyloxycarbonyl)methoxy]imino]acetic acid, melting at 175° C. (dec.), is obtained.

1.9 g of the above acetic acid derivative in 30 ml of acetonitrile are stirred with 1.4 ml of N-methylmorpholine, 2.0 g of 2,2-dithio-bis-benzothiazole and 1.14 ml of triethylphosphite. After stirring for 1 hour at room temperature the reaction mixture is cooled to 0° C. and filtered. The filtrate is evaporated to dryness and the residue crystallized from methylene chloride. 2-(2-Amino-4-thiazolyl)-2-[[(Z)-(p-nitrobenzyloxycarbonyl)methoxy]imino]acetic acid-2-benzothiazolyl-thioester is obtained melting at 124°–126° C.

EXAMPLE 12 cis-3-Amino-4-methoxycarbonyl-1-(2,4-dimethoxybenzyl)-2-azetidinone (23.54 g) and di-(p-toluoyl)-D-tartaric acid monohydrate (16.17 g) are added to 600 ml of acetonitrile, and the mixture is warmed for dissolution, filtered and allowed to cool. The resulting crystalline precipitate is collected by filtration and washed with cold acetonitrile to give the salt (20.3 g). Recrystallization from 300 ml of acetonitrile gave 16.3 g of the salt.

M.p. 165°–168° C.

$[\alpha]_D^{22} +71.9°$ (c=0.985, MeOH).

The above salt is dissolved in a mixture of 100 ml of water and 300 ml of tetrahydrofuran, followed by addition of 6.1 g of sodium hydrogen carbonate. Then, under ice-cooling and stirring, 4.2 ml of carbobenzoxy chloride is added dropwise. The mixture is stirred under ice-cooling for an hour and then at room temperature for an hour, and the tetrahydrofuran is distilled off under reduced pressure on a water bath at not higher than 30° C. The residue is shaken with 400 ml of ethyl acetate and 200 ml of water and the aqueous layer is reextracted with 200 ml of ethyl acetate. These extracts are combined and washed twice with 2% aqueous solution of sodium bicarbonate then with aqueous sodium chloride, 1N hydrochloric acid and aqueous sodium chloride in that order, and dried. The solvent is then distilled off under reduced pressure and 30 ml of ether is added. The resulting crystalline precipitate is collected by filtration and dissolved in 50 ml of ethyl acetate by warming. After filtration, 50 ml of hexane is added to the filtrate and the mixture is allowed to cool. The colorless crystalline precipitate is collected by filtration to give 6.45 g (37.5%) of (3S,4S)-cis-3-benzyloxycarboxamido-4-methoxycarbonyl-1-(2,4-dimethoxybenzyl)-2-azetidinone.

M.p. 120°–121° C.,
$[\alpha]_D^{22} +24.4°$ (c=1.08, CHCl$_3$),
IR$\nu_{max}^{Nujol}$ cm$^{-1}$: 3300, 1770, 1745, 1695.

Elemental analysis:

|  | Calcd. for C$_{22}$H$_{24}$N$_2$O$_7$: | | |
|---|---|---|---|
|  | C (%) | H (%) | N (%) |
|  | 61.67 | 5.65 | 6.54 |
| Found: | 61.50 | 5.59 | 6.37 |

EXAMPLE 13

(3S,4S)-cis-3-Benzyloxycarboxamido-4-methoxycarbonyl-1-(2,4-dimethoxybenzyl)-2-azetidinone (12.8 g) is dissolved in 300 ml of tetrahydrofuran and, under ice-cooling and stirring, a solution of 2.8 g of sodium borohydride in 150 ml of cold water is added dropwise over 10 minutes. After completion of addition, the mixture is stirred under ice-cooling for an hour and at room temperature for 3 hours. The tetrahydrofuran is distilled off on a water bath at not higher than 30° C. under reduced pressure and water is added to the residue. After filtration, the solid matter on the filter is washed with water and ethyl acetate to give 4.4 g of crude crystals. The mother liquor and washings are combined and shaken and the ethyl acetate layer is separated. The aqueous layer is reextracted with ethyl acetate hese ethyl acetate layers are combined, washed with 1N hydrochloric acid and aqueous sodium chloride, dried over anhydrous sodium sulfate, and concentrated under reduced pressure. The residue and the above-obtained crude crystals are combined and recrystallized from ethyl acetate to give 9.1 g (76%) of (3S,4S)-cis-3-benzyloxycarboxamido-1-(2,4-dimethoxybenzyl)-4-hydroxymethyl-2-azetidinone as colorless crystals.

M.p. 137°–138° C.
$[\alpha]_D^{25} -32.7°$ (c=1, CHCl$_3$).
IR$\nu_{max}^{Nujol}$ cm$^{-1}$: 3480, 3345, 1740, 1715, 1695.
NMR(CDCl$_3$)δ: 3.5–3.9(3H, C$_4$—H, C$_4$—CH$_2$), 3.78(3H, s, OCH$_3$), 3.79(3H, s, OCH$_3$), 4.35(2H, s, N$_1$—CH$_2$), 4.9–5.2(1H, m, C$_3$—H), 5.07(2H, s, CH$_2$ ph), 6.06(1H, d, J=10 Hz, C$_3$—NH), 6.3–6.6(2H, m, aromatic protons) 7.1–7.3(1H, m, aromatic protons) 7.32(5H, s, ph).

Elemental analysis:

|  | Calcd. for C$_{21}$H$_{24}$N$_2$O$_6$: | | |
|---|---|---|---|
|  | C (%) | H (%) | N (%) |
|  | 62.99 | 6.04 | 7.00 |
| Found: | 62.92 | 5.90 | 7.03 |

EXAMPLE 14

(3S,4S)-cis-3-Benzyloxycarboxamido-1-(2,4-dimethoxybenzyl)-4-hydroxymethyl-2-azetidinone (2.0 g) is dissolved in 40 ml of methylene chloride and, under ice-cooling and stirring, 0.52 ml of chlorosulfonyl isocyanate is added. The mixture is stirred under ice-cooling for 30 minutes and 0.35 ml of chlorosulfonyl isocyanoate is added. The mixture is further stirred for 10 minutes and, under ice-cooling, a solution of 1.26 g of sodium sulfite in 30 ml of water is added. The whole mixture is stirred at room temperature for an hour. The methylene chloride is then distilled off under reduced pressure and the residue is extracted with chloroform. The extract is washed with aqueous sodium chloride and dried over anhydrous magnesium sulfate. The solvent is distilled off under reduced pressure, followed by addition of ether and filtration to give 2.46 g of crude crystals. Recrystallization from ethyl acetate-hexane gives 1.72 g (77.7%) of (3S,4S)-cis-3-benzyloxycarboxamido-4-carbamoyloxymethyl-1-(2,4-dimethoxybenzyl)-2-azetidinone as colorless crystals.

M.p. 179°–180° C.
$[\alpha]_D^{24.5} +34.5°$ (c=0.8, DMSO).
IR$\nu_{max}^{KBr}$ cm$^{-1}$: 3410, 3300, 1760, 1710.
NMR(d$_6$—DMSO)δ: 3.74(3H, s, O CH$_3$), 3.76(3H, s, OCH$_3$), 3.7–4.3 (3H, m, C$_4$—H, C$_4$—CH$_2$), 4.20(2H, ABq, J=15 Hz, N$_1$—CH$_2$), 4.92(1H, d.d, J=5, 10 Hz, C$_3$—H), 5.05(2H, s, CH$_2$ph), 7.35(5H, s, ph), 7.87(1H, d, J=10 Hz, C$_3$—NH).

Elemental analysis:

|  | for C$_{22}$H$_{25}$N$_3$O$_7$: | | |
|---|---|---|---|
|  | C (%) | H (%) | N (%) |
| Calcd. | 59.59 | 5.68 | 9.48 |
| Found: | 59.80 | 5.70 | 9.57 |

EXAMPLE 15

(3S,4S)-cis-3-Benzyloxycarboxamido-4-carbamoyloxymethyl-1-(2,4-dimethoxybenzyl)-2-azetidinone (1.60 g), potassium persulfate (1.41 g) and dipotassium phosphate (0.85 g) are suspended in a mixture of acetonitrile (36 ml) and water (18 ml) and the suspension is stirred in an argon atmosphere on a water bath at 95° C. for 80 minutes. The acetonitrile is distilled off under reduced pressure and 10 ml of aqueous sodium chloride is added, followed by extraction with ethyl acetate-tetrahydrofuran. The extract is washed with 5% aqueous sodium bicarbonate and aqueous sodium chloride and dried over anhydrous magnesium sulfate. The solvent is then distilled off under reduced pressure and the solid residue is recrystallized from ethyl acetate to give 426 mg (40.3%) of (3S,4S)-cis-benzyloxycarboxamido-4-carbamoyloxymethyl-2-azetidinone as pale yellow crystals. The mother liquor is concentrated and the residue is purified by silica gel column chromatography [70 g; eluent: CHCl$_3$—MeOH—ethyl acetate (85:10:5) to give 353 mg of crystals (colorless) as a second crop.

Overall yield 779 mg (73.6%).
M.p. 191°–192° C.
$[\alpha]_D^{25} +60.6°$ (c=1, MeOH).
IR$\nu_{max}^{KBr}$ cm$^{-1}$: 3400, 3300, 1755 (sh), 1745, 1695.
NMR(d$_6$—DMSO)δ: 3.70–4.25(3H, C$_4$—H, C$_4$—CH$_6$), 4.95(1H, d.d, J=5, 10 Hz, C$_3$—H), 5.05(2H, s, CH$_2$ ph), 6.47(2H, br. s, CONH$_2$) 7.33(5H, s, ph), 7.92(1H, d, J=10 Hz, C$_3$—NH), 8.30(1H, br. s, N$_1$—H).

Elemental analysis:

| | Calcd. for C₁₃H₁₅N₃O₅: | | |
|---|---|---|---|
| | C (%) | H (%) | N (%) |
| | 53.23 | 5.15 | 14.32 |
| Found: | 52.83 | 5.02 | 14.26 |

EXAMPLE 16

(3S,4S)-cis-3-Benzyloxycarboxamido-4-carbamoyloxymethyl-2-azetidinone (293 mg) as obtained in Example 15 is dissolved in 10 ml of dioxane, 477 mg of sulfuric anhydride-pyridine complex is added, and the mixture is stirred at room temperature for 14 hours. The dioxane is distilled off under reduced pressure and the residue is stirred with 20 ml of water and 20 ml of Dowex 50W (Na) at room temperature for an hour. The resin is then filtered off and the filtrate is concentrated under reduced pressure. The residue is subjected to chromatography on an Amberlite XAD-2 column and elution is carried out with water, 5% ethanol and 10% ethanol in that order. The fractions containing the desired product are combined, concentrated under reduced pressure and lyophilized to give 270 mg (64%) of sodium (3S,4S)-cis-3-benzyloxycarboxamido-4-carbamoyloxymethyl-2-azetidinone-1-sulfonate as a colorless powder.

$[\alpha]_D^{25} +29.4°$ (c=0.715, H₂O).

IR$\nu_{max}^{KBr}$ cm⁻¹: 3500, 3370, 3320, 1795, 1760, 1730, 1690.

NMR(d₆—DMSO)δ: 3.85–4.40(3H, C₄—H, C₄—CH₂), 4.92(1H, d,d, J=5, 10 Hz, C₃—H), 6.10–6.65(1H, CONH₂, 7.35(5H, s, Ph), 7.98 (1H, d, J=10 Hz, C₃—NH).

Elemental analysis:

| | for C₁₃H₁₄N₃NaO₈S.1½H₂O: | | |
|---|---|---|---|
| | C (%) | H (%) | N (%) |
| Calcd.: | 36.97 | 4.06 | 9.95 |
| Found: | 37.24 | 4.13 | 10.02 |

The above product (236 mg) is dissolved in 6.7 ml of water, 0.56 ml of 1N hydrochloric acid and 236 mg of 10% palladium-on-carbon are added thereto, and the mixture is stirred in a hydrogen atmosphere at room temperature for 40 minutes. The catalyst is then filtered off and washed with 16 ml of water. The filtrate and washings are combined and concentrated to 4 ml under reduced pressure, followed by addition of 2.24 ml of 1N hydrochloric acid. The resulting mixture is further concentrated to 1 ml and then allowed to stand in a refrigerator at 4° C. overnight. The resulting colorless crystals are collected by filtration, washed with 1 ml of cold water and dried over phophorus pentoxide under reduced pressure to give 80 mg (60%) of (3S,4S)-cis-3-amino-4-carbamoyloxymethyl-2-azetidinone-1-sulfonic acid.

M.p. 207°–210° C. (decompn.).

$[\alpha]_D^{24} -62.9°$ (C=0.49, DMSO).

IR(KBr)cm⁻¹: 3440, 3350, 3180, 1795, 1775, 1735, 1720.

NMR (d₆—DMSO)δ: 4.67(1H, d, J=5 Hz, C₃—H).

Elemental analysis:

| | for C₅H₉N₃O₆S: | | |
|---|---|---|---|
| | C (%) | H (%) | N (%) |
| Calcd.: | 25.10 | 3.79 | 17.57 |
| Found: | 25.02 | 3.72 | 17.73 |

EXAMPLE 17 cis-3-Benzyloxycarboxamido-1-(2,4-dimethoxybenzyl)-4-hydroxymethyl-2-azetidinone (racemic form) is worked up in the same manner as Examples 14 and 15 to give cis-3-benzyloxycarboxamido-4-carbamoyloxymethyl-2-azetidinone (racemic form), which, on recrystallization from acetone-ethyl acetate, melts at 210°–211° C.

This product (1.45 g) is suspended in 87 ml of dioxane, 1.753 g of sulfuric anhydride-pyridine complex is added, and the mixture is stirred at room temperature for 7 hours. The dioxane is distilled off under reduced pressure and the residue is stirred with 100 ml of water and 45 ml of Dowex 50W (Na) for an hour. The resin is then filtered off and the filtrate is concentrated to 20 ml under reduced pressure to give a crystalline precipitate. After cooling, the crystals are collected by filtration and dried to give 1.52 g (74.5%) of sodium cis-3-benzyloxycarboxamido-4-carbamoyloxymethyl-2-azetidinone-1-sulfonate.

M.p. 167°–169° C. (decompn.).

IR (KBr) cm⁻¹: 3500, 3350, 1790, 1690.

NMR (d₆—DMSO)δ: 4.93(1H, d.d, J=6, 9 Hz, C₃—H), 5.07(2H, s, CH₂ph), 7.39(5H, s, ph), 7.99(1H, d, J=9 Hz), C₃NH).

Elemental analysis:

| | for C₁₃H₁₄N₃NaO₈S.H₂O: | | |
|---|---|---|---|
| | C (%) | H (%) | N (%) |
| Calcd.: | 37.78 | 3.90 | 10.17 |
| Found: | 37.81 | 3.98 | 10.07 |

EXAMPLE 18

Sodium cis-3-benzyloxycarboxamido-4-carbamoyloxymethyl-2-azetidinone-1-sulfonate monohydrate (1.0 g) is suspended in 34 ml of water and the suspension is adjusted to pH 2 with 1N hydrochloric acid. Then, 1.0 g of 10% palladium-on-carbon is added and the mixture is stirred in a hydrogen atmosphere at room temperature for an hour and then adjusted again to pH 2 with 1N hydrochloric acid. The catalyst is filtered off and the filtrate is concentrated to 5 ml under reduced pressure. Under ice-cooling, 9.68 ml of 1N hydrochloric acid is added and the mixture is stirred for 30 minutes, whereupon crystals separate out. The mixture is concentrated to 2 ml under reduced pressure and allowed to stand in a refrigerator overnight. The crystals are collected by filtration, washed with a small amount of cold water and dried to give 454 mg of cis-3-amino-4-carbamoyloxymethyl-2-azetidinone-1-sulfonic acid.

M.p. 209°–211° C. (decompn.)

IR (KBr)cm⁻¹: 3450, 3350, 3150, 2980, 1780, 1760, 1720, 1610, 1530, 1055.

What is claimed is:

1. A compound of the formula

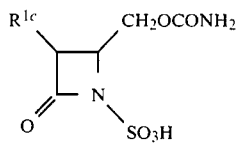

wherein $R^{1c}$ is amino or protected amino, or a base addition or acid addition salt or ester thereof.

2. A compound as claimed in claim 1, wherein $R^{1c}$ is amino group.

3. A compound as claimed in claim 1, wherein $R^{1c}$ is a protected amino group.

4. A compound as claimed in claim 3, wherein the protecting group of the protected amino group is an aromatic acyl, aliphatic acyl, esterified carboxyl, trityl or trialcyloilyl amino-protecting group.

5. A compound as claimed in claim 3, wherein the protecting group of the protected amino group is an esterified carboxyl group.

6. A compound as claimed in claim 5, wherein the esterified carboxyl group is benzyloxycarbonyl.

7. A compound as claimed in claim 1, wherein the group represented by the symbol $R^{1c}$ has $\beta$-configuration to the azetidine ring.

8. A compound as claimed in claim 1, which is sodium cis-3-benzyloxycarboxamido-4-carbamoyloxymethyl-2-azetidinone-1-sulfonate.

9. A compound as claimed in claim 1, which is sodium (3S,4S)-cis-3-benzyloxycarboxamido-4-carbamoyloxymethyl-2-azetidinone-1-sulfonate.

10. A compound as claimed in claim 1, which is cis-3-amino-4-carbamoyloxymethyl-2-azetidinone-1-sulfonic acid.

11. A compound as claimed in claim 1, which is (3S,4S)-cis-3-amino-4-carbamoyloxymethyl-2-azetidinone-1-sulfonic acid.

* * * * *

UNITED STATES PATENT AND TRADEMARK OFFICE
CERTIFICATE OF CORRECTION

PATENT NO. : 4,673,739

DATED : June 16, 1987

INVENTOR(S) : TAISUKE MATSUO, MICHIHIKO OCHIAI and SHOJI KISHIMOTO

It is certified that error appears in the above-identified patent and that said Letters Patent is hereby corrected as shown below:

Claim 4, line 21, correct the spelling of "trialkylsilyl".

Signed and Sealed this

Twenty-fourth Day of November, 1987

Attest:

DONALD J. QUIGG

Attesting Officer

Commissioner of Patents and Trademarks